(12) United States Patent
Maekawa et al.

(10) Patent No.: US 11,067,493 B2
(45) Date of Patent: Jul. 20, 2021

(54) PARTICLE MEASURING METHOD, SAMPLE PROCESSING METHOD, AND PARTICLE IMAGING APPARATUS

(71) Applicant: SYSMEX CORPORATION, Kobe (JP)

(72) Inventors: Takanori Maekawa, Kobe (JP); Yusuke Konishi, Kobe (JP)

(73) Assignee: SYSMEX CORPORATION, Hyogo (JP)

( * ) Notice: Subject to any disclaimer, the term of this patent is extended or adjusted under 35 U.S.C. 154(b) by 8 days.

(21) Appl. No.: 16/211,469

(22) Filed: Dec. 6, 2018

(65) Prior Publication Data

US 2019/0178782 A1 Jun. 13, 2019

(30) Foreign Application Priority Data

Dec. 8, 2017 (JP) .............................. JP2017-236445
Jul. 20, 2018 (JP) .............................. JP2018-136744

(51) Int. Cl.
*C12Q 1/6806* (2018.01)
*C12Q 1/686* (2018.01)
*G01N 33/58* (2006.01)
*C12Q 1/6841* (2018.01)
*G01N 33/53* (2006.01)
(Continued)

(52) U.S. Cl.
CPC ....... *G01N 15/1404* (2013.01); *C12Q 1/6806* (2013.01); *C12Q 1/686* (2013.01); *C12Q 1/689* (2013.01); *C12Q 1/6841* (2013.01); *C12Q 1/6883* (2013.01); *G01N 15/14* (2013.01); *G01N 15/1459* (2013.01); *G01N 33/53* (2013.01); *G01N 33/533* (2013.01);
*G01N 33/56916* (2013.01); *G01N 33/56972* (2013.01); *G01N 33/582* (2013.01); *C12Q 2600/158* (2013.01);
(Continued)

(58) Field of Classification Search
CPC .............................. C12Q 1/6841; C12Q 1/686
See application file for complete search history.

(56) References Cited

U.S. PATENT DOCUMENTS 5,843,640 A * 12/1998 Patterson .......... G01N 33/56972
435/5

FOREIGN PATENT DOCUMENTS

WO WO 2015/200717 A2 12/2015
WO WO 2015/200717 A3 4/2016

OTHER PUBLICATIONS

Janiszewska, M. et al., In situ single-cell analysis identifies heterogeneity for PIK3CA mutation and HER2 amplification in HER2-positive breast cancer, Nature Genet., vol. 47, pp. 1212-1219 and online methods pp. 1-3 (Year: 2015).*
(Continued)

*Primary Examiner* — Teresa E Strzelecka
(74) *Attorney, Agent, or Firm* — Brinks Gilson & Lione

(57) ABSTRACT

A particle measuring method, a sample processing method, and a particle imaging apparatus capable of efficiently acquiring information effective in pathological diagnosis or the like are provided. The particle measuring method comprises a step (S13) of labeling and amplifying, within a particle, a target nucleic acid in the particle, a step (S14) of labeling a surface target polypeptide on the surface of the particle and/or target nucleic acid different from the first target nucleic acid, and a step (S2) of measuring the labeled target nucleic acid and the labeled target polypeptide and/or other labeled target nucleic acid.

14 Claims, 16 Drawing Sheets

(51) Int. Cl.
　　*G01N 15/14*　　(2006.01)
　　*C12Q 1/6883*　　(2018.01)
　　*G01N 33/569*　　(2006.01)
　　*C12Q 1/689*　　(2018.01)
　　*G01N 33/533*　　(2006.01)

(52) U.S. Cl.
　　CPC .................. *G01N 2333/245* (2013.01); *G01N 2333/70589* (2013.01)

(56) References Cited

OTHER PUBLICATIONS

Ramage, G. et al., Combined fluorescent in situ hybridization and immunolabeling of Bacteroides fragilis, J. Immunol. Meth., vol. 212, pp. 139-147 (Year: 1998).*

Ke, R. et al., In situ sequencing for RNA analysis in preserved tissue and cells, Nature Meth., vol. 10, pp. 857-860, plus online methods pp. 1-2 (Year: 2013).*

Ke, R. et al., In situ sequencing for RNA analysis in preserved tissue and cells, Nature Meth., vol. 10, supplemental material pp. 1-29 (Year: 2013).*

Kurokawa et al., "Detection of intestinal hemorrhagic *E. coli* by in situ PCR method", Journal of Japanese bacteriology, 52 (2), 513-518, 1997.

Testoni et al., "A New Method of "In-Cell Reverse Transcriptase-Polymerase Chain Reaction" for the Detection of BCR/ABL Transcript in Chronic Myeloid Leukemia Patients", Blood, vol. 87, No. 9, dated May 1, 1996, pp. 3822-3827.

Eastburn et al., "Identification and genetic analysis of cancer cells with PCR-activated cell sorting" Nucleic Acids Research, vol. 42, No. 16, dated Jul. 16, 2014, pp. e128-e128, 10 pages.

Shembekar et al., "Droplet-based microfluidics in drug discovery, transcriptomics and high-throughput molecular genetics" Lab on a Chip, vol. 16, No. 8, dated Jan. 1, 2016, pp. 1314-1331.

Pellegrino et al., "RNA-Seq following PCR-based sorting reveals rare cell transcriptional signatures" BMC Genomics, vol. 17, No. 361, dated May 17, 2016, 12 pages.

Lim et al., "PCR-activated cell sorting as a general, cultivation-free method for high-throughput identification and enrichment of virus hosts" Journal of Virological Methods, Elsevier BV, NL, vol. 242, dated Dec. 29, 2016, pp. 14-21.

Manti et al., "Experimental improvements in combining CARD-FISH and flow cytometry for bacterial cell quantification" Journal of Microbiological Methods, Elsevier, Amsterdam, NL, vol. 87, No. 3, dated Sep. 8, 2011, pp. 309-315.

Andreas P Frei et al: "Highly multiplexed simultaneous detection of RNAs and proteins in single cells", Nature Methods, Published online on Jan. 25, 2016, vol. 13, No. 3, pp. 269-275.

Sunjong Kwon et al: "Quantitative, in situ analysis of mRNAs and proteins with subcellular resolution", Scientific Reports, Published online on Nov. 28, 2017, vol. 7, Article No. 16459, 11 pages.

The Communication pursuant to Article 94(3) EPC dated Sep. 2, 2020 in a counterpart European patent application No. 18210067.7.

* cited by examiner

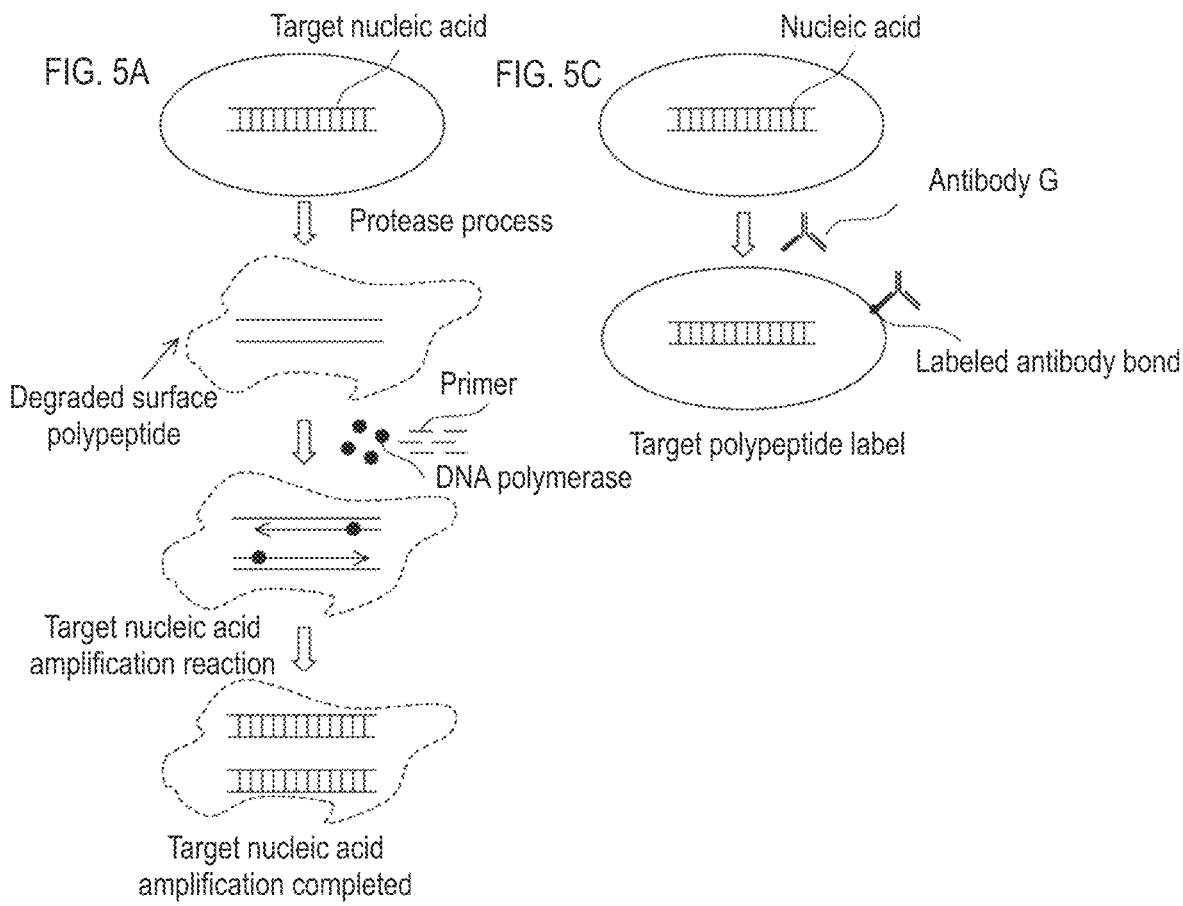
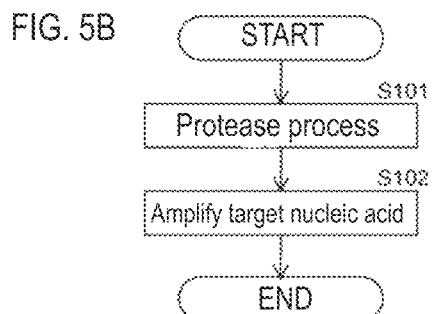
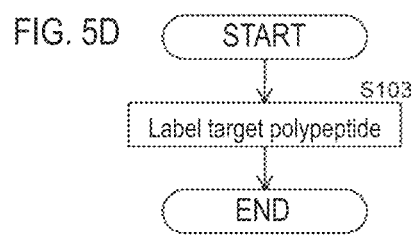

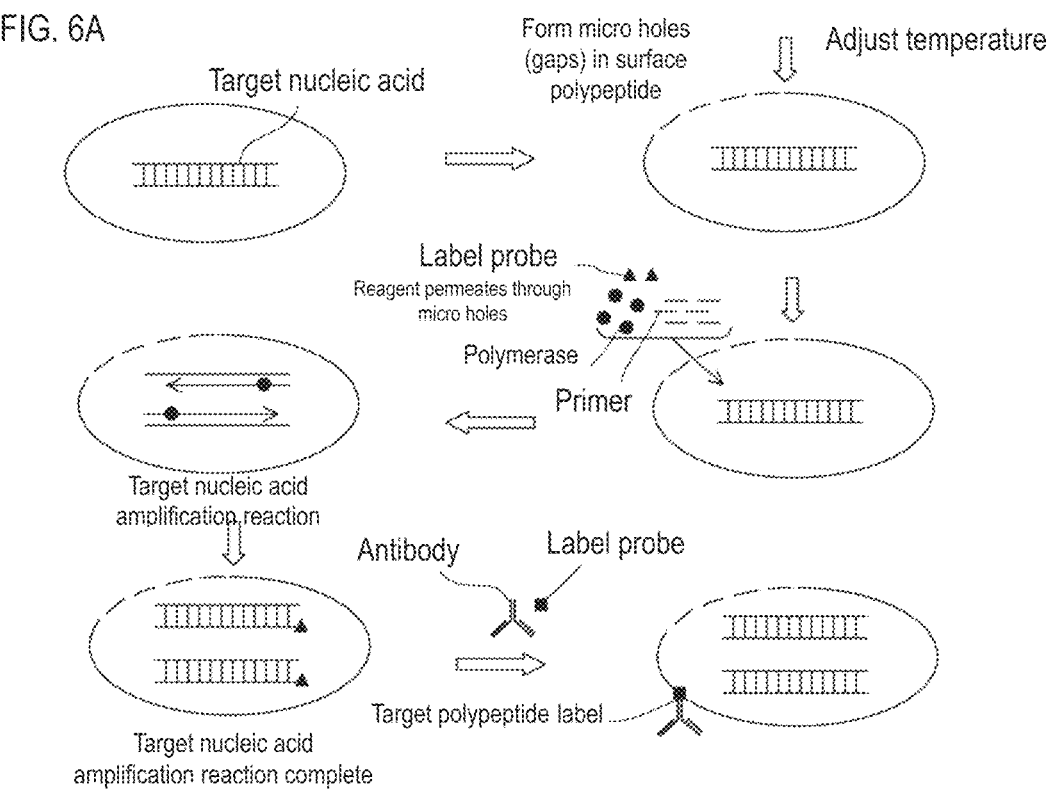

FIG. 8
| | Bright field image | Target nucleic acid | Target polypeptide | Target nucleic acid and target polypeptide mix |
|---|---|---|---|---|
| Measurement 1 |  | 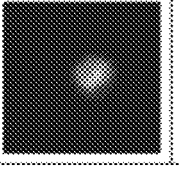 | 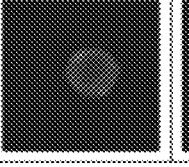 | 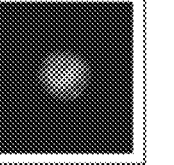 |

FIG. 11
| | Bright field image | Target nucleic acid | Target polypeptide | Target nucleic acid and target polypeptide mix |
|---|---|---|---|---|
| Measurement 9 | 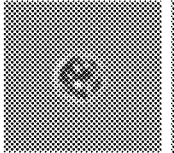 | 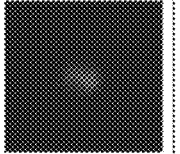 | 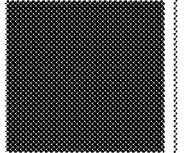 | 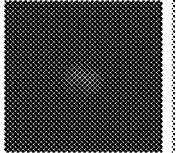 |

Measurement 10: Exosome super resolution

FIG. 14
| | Bright field image | Target nucleic acid | Target polypeptide | Target nucleic acid and target polypeptide mix |
|---|---|---|---|---|
| Measurement 12 |  | 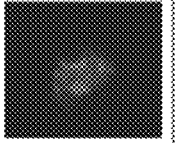 | 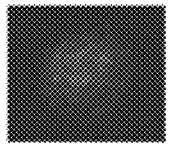 | 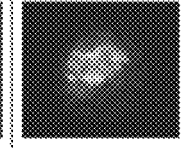 |

PARTICLE MEASURING METHOD, SAMPLE PROCESSING METHOD, AND PARTICLE IMAGING APPARATUS

RELATED APPLICATIONS

This application claims priority from prior Japanese Patent Application No. 2017-236445, filed on Dec. 8, 2017, entitled "Particle Measuring Method, Sample Processing Method, and Particle Imaging Apparatus", and prior Japanese Patent Application No. 2018-136744, filed on Jul. 20, 2018, entitled "Particle Measuring Method, Sample Processing Method, and Particle Imaging Apparatus", the entire contents of which are incorporated herein by reference.

BACKGROUND OF THE INVENTION

1. Field of the Invention

The present invention relates to a particle measuring method, a sample processing method, and a particle imaging apparatus.

2. Description of the Related Art

An in situ PCR method of amplifying a target nucleic acid as a target nucleic acid is employed as a method of detecting abnormal cells. Kurokawa et al., "Detection of intestinal hemorrhagic E. coli by in situ PCR method", Journal of Japanese bacteriology, 52 (2), 513-518, 1997 discloses an experiment for detecting a specific nucleic acid in *Escherichia coli*. As shown in FIG. 16, in this experiment, the operator fixes *E. coli* with formalin, then treats *E. coli* with protease causing the reagents such as thermostable DNA polymerase and primers to penetrate into *E. coli* and amplify the target nucleic acid. The operator confirms the presence of the target nucleic acid with a fluorescence microscope. As described above, the in situ PCR method can reliably detect the target nucleic acid by amplifying the target nucleic acid.

SUMMARY OF THE INVENTION

When an abnormality is present in cells, bacteria and the like and the cause is nucleic acid, the method disclosed in Non-Patent Document 1 is effective. However, when the cause of the abnormality is not a nucleic acid, other causes may include abnormalities of polypeptides such as proteins. Alternatively, abnormalities may be present in both nucleic acids and polypeptides.

For example, when the cause of an abnormality is plurality of nucleic acids contained in a cell, it is important to find the abnormality by using an effective detection method for each nucleic acid in order to perform appropriate pathological diagnosis.

The present invention provides a particle measuring method, a sample processing method, and a particle imaging apparatus capable of efficiently acquiring information effective in pathological diagnosis and the like.

A first aspect of the present invention relates to a particle measuring method. The particle measuring method according to this aspect includes a step (S13) of labeling and amplifying, within the particle, a target nucleic acid in the particle, a step (S14) of labeling a target polypeptide and/or other target nucleic acid different from the first target nucleic acid of the particle, and a step (S2) of measuring the labeled target nucleic acid and the labeled target polypeptide and/or other labeled target nucleic acid.

"Particle" means cells, bacteria and the like contained in a specimen. The particles to be measured also may be exosomes or the like of the endoplasmic reticulum. The "specimen" mentioned above means blood specimen collected directly from a person, a piece of tissue such as skin, and the like. "Polypeptide" is a molecule in which amino acid residues are linked by peptide bonds, and includes, for example, an amino acid polymer having a relatively small molecular weight and a protein having a large molecular weight.

"Labeling and amplifying a target nucleic acid" also is not limited to merely meaning to amplify a nucleic acid, that is, DNA or messenger RNA (mRNA) present in a particle. For example, in the exosome which is one of the extracellular vesicles that have been actively studied in recent years, noncoding RNA (ncRNA) such as microRNA (miRNA) and nucleic acids controlled by them are also included. Amplifying the target nucleic acid is not limited to amplifying this miRNA, inasmuch as the nucleic acid transcribed from the miRNA also may be amplified. In the particle measuring method according to this aspect, all the particles including the nucleic acid as described above are to be measured. Hereinafter, "labeling and amplifying a target nucleic acid" is described as meaning the same.

"Other target nucleic acid" means one target nucleic acid among two target nucleic acids having mutually different gene information. "Other target nucleic acid" also means one of the two mutually different regions in the nucleotide sequence of a nucleic acid. The above target nucleic acid and other target nucleic acid may be double stranded or single stranded. According to the particle measuring method of this aspect, labeling and amplifying a target nucleic acid and labeling of a target polypeptide can be simultaneously performed on one cell, or labeling of two different target nucleic acids with respect to one cell can be performed at the same time. According to the above-described configuration, effective information can be obtained in pathology diagnosis and the like since it is possible to complementarily associate the information on the presence or absence of abnormality of nucleic acid and the presence or absence of abnormality of the polypeptide, or the presence or absence of abnormality of two different nucleic acids for one cell.

In the particle measuring method according to this aspect, either of the labeling of the target nucleic acid and the amplification of the target nucleic acid may be performed first. Hereinafter, "labeling and amplifying a target nucleic acid" is the same.

In the particle measuring method according to this aspect, the target polypeptide on the surface of the particle is labeled in step (S14) of labeling the target polypeptide of the particle and/or other target nucleic acid different from the first target nucleic acid, and the labeled target nucleic acid and labeled target polypeptide are measured in step (S2) of measuring the labeled target nucleic acid and labeled target polypeptide and/or labeled target other nucleic acid.

According to the particle measuring method of this aspect, amplification and labeling of a target nucleic acid and labeling of a target polypeptide can be simultaneously performed on one cell. The reliability of evaluation on one cell is improved since information on both the presence and absence of abnormality of a nucleic acid and the presence or absence of abnormality of a polypeptide can be obtained for one cell.

In the particle measuring method according to this aspect, the step (S2) of measuring the labeled target nucleic acid and the labeled target polypeptide and/or other target nucleic acid is performed after the step (S13) of labeling and amplifying, within the particle, the target nucleic acid in the particle, and the step (S14) of labeling a target polypeptide and/or other target nucleic acid different from the first target nucleic acid of the particle.

As a method for measuring a labeled target nucleic acid and a labeled target polypeptide or other target nucleic acid, this method is, for example, a method in which a measurement sample, that is, a fluid containing a labeled target nucleic acid, a labeled target polypeptide or labeled other target nucleic acid flows through a flow cell and is irradiated by light from a light source whereupon the light given off from the fluid is imaged, and a method of imaging with a fluorescence microscope. By such measurement, it is possible to evaluate whether amplification of the target nucleic acid and labeling of the target polypeptide or amplification of other target nucleic acid have been performed relative to the same particle.

In the particle measuring method according to this aspect, it is preferable to include a step of capturing an image of the particle in the step (S2) of measuring the labeled target nucleic acid and the labeled target polypeptide and/or other target nucleic acid.

In this way the operator can visually confirm the presence or absence of amplification of the target nucleic acid and the presence or absence of amplification of the target polypeptide or other target nucleic acid.

In the particle measuring method according to this aspect, the step (S2) of measuring the labeled target nucleic acid and the labeled target polypeptide and/or other target nucleic acid is configured to flow a fluid including a labeled target nucleic acid and a target polypeptide and/or other target nucleic acid into a flow cell (10) and imaging the light obtained by irradiating the liquid in the flow cell (10) with light.

In this way it is possible to determine whether the cause of an abnormality is a nucleic acid, a polypeptide, or both for a large amount of particles. Alternatively, it can be determined whether an abnormality has occurred by mutually different nucleic acids. Hence, the reliability of the measurement result is improved.

In the particle measuring method according to this aspect, after the step (S2) of measuring the labeled target nucleic acid and the labeled target polypeptide and/or other target nucleic acid, a step (S3) of analyzing the obtained image is performed.

In this way it is possible to accurately evaluate whether the cause of an abnormality of particles is nucleic acid, polypeptide, or both based on the captured image. Alternatively, it is possible to accurately evaluate whether an abnormality has occurred due to mutually different nucleic acids.

In the particle measuring method according to this aspect, the target nucleic acid is labeled with a first labeling substance (S13), and the target polypeptide and/or other target nucleic acid is labeled with a second labeling substance different from the first labeling substance (S14).

In this way, by labeling each of the target nucleic acid and the target polypeptide or other target nucleic acid, it is possible to appropriately determine whether the target nucleic acid is amplified, whether the target polypeptide is labeled with a labeling substance, and whether the other target nucleic acid has been amplified.

In the particle measuring method according to this aspect, a mixed solution containing particles and the labeling substance for labeling the target nucleic acid is prepared in step (S13) of labeling and amplifying, in the particle, the target nucleic acid in the particle. In this case, the mixture can be prepared to be substantially free of proteases.

When preparing a mixed solution for amplification of a target nucleic acid in a state where a protease is contained in the mixed solution, a polypeptide on the surface of the particle will decompose through the action of the protease. It is not possible to label a target polypeptide relative to particles in such a mixed solution. On the other hand, when the preparation of the mixed solution is carried out in a state substantially free of protease, a polypeptide on the surface of a particle is not completely decomposed. In this way, the target polypeptide can be labeled with the particle measuring method according to this aspect. In this way information based on the target polypeptide can be obtained at the same time as information based on the target nucleic acid is acquired from one particle. Hence, particle evaluation can be performed more accurately.

In this case, the mixed solution is prepared to contain a polymerase, and may be prepared to also include a primer. In this way a reagent necessary for amplification of the target nucleic acid is added to the mixed solution, and amplification of the target nucleic acid in the particle can proceed appropriately.

In the particle measuring method according to this aspect, it is possible to perform step (S13) of labeling and amplifying, within a particle, a target nucleic acid in the particle in the particle after setting the temperature of the liquid containing the particle at 25° C. or more and 95° C. or less (S12).

When the liquid containing particles is adjusted to such a temperature range, the gap of polypeptides on the surface of the particle expands, but the polypeptide is not completely decomposed. Therefore, the particles remain in the liquid while maintaining the shape of the polypeptide on the surface. As the gap widens, the reagent permeates efficiently into the inside of the particle. Hence, the amplification of the target nucleic acid proceeds smoothly since the reagent necessary for the amplification of the target nucleic acid is sufficiently present inside the particle. As described above, a target polypeptide can be labeled relative to the same particle since the particle is not completely decomposed.

In the particle measuring method according to this aspect, it is possible to carry out step (S13) of labeling and amplifying, within the particle, the target nucleic acid in the particle after setting the temperature of the particle-containing liquid to 25° C. or more and 75° C. or less (S12).

When the liquid containing particles is adjusted to such a temperature range, the particles remain in the liquid while maintaining the shape of the surface polypeptides, and the reagents penetrate to the interior of the particles more efficiently. Hence, the amplification reaction of the target nucleic acid proceeds more smoothly. As described above, a target polypeptide also can be labeled relative to the same particle since the surface polypeptide of the particle is not completely decomposed.

In the particle measuring method according to this aspect, after step (S13) of labeling and amplifying the target nucleic acid, a step (S14) of labeling a target polypeptide and/or other target nucleic acid can be performed.

In this way, after amplifying the target nucleic acid, a step of labeling a target polypeptide or a step of labeling another target nucleic acid with respect to the same particle allows information of the target nucleic acid and the target polypeptide or other target nucleic acid to be acquired at once. Hence, the reliability of the evaluation for one particle increases.

In the particle measuring method according to this aspect, the step (S14) of labeling the target polypeptide and/or other target nucleic acid that is different from the first target nucleic acid performs labeling the target polypeptide with a labeled antibody that specifically binds to the target polypeptide.

In this way it is possible to appropriately determine whether the target polypeptide of interest is contained on the surface or inside of the particle.

In the particle measuring method according to this aspect, the step (S14) of labeling the target polypeptide of the particle and/or other target nucleic acid different from the first target nucleic acid is carried out by labeling the target polypeptide contained in the particle, is configured to measure the labeled target nucleic acid and the labeled target polypeptide in step (S2) of measuring the nucleic acid and the labeled target polypeptide and/or other target nucleic acid.

"Target polypeptide contained in the particle" means a target polypeptide located on the surface of the particle and a target polypeptide present within the particle.

According to the particle measuring method of this aspect, amplification and labeling of a target nucleic acid and labeling of a target polypeptide can be simultaneously performed on one cell. The cause of a disease may be a combination of multiple genetic abnormalities. Therefore, sufficient diagnosis cannot be made with information relating to only one target nucleic acid. With the configuration of this aspect, it is possible to investigate the presence of an abnormality in the target nucleic acid and the target polypeptide contained in one cell. By associating these pieces of information complementarily, it is possible to obtain effective information for pathological diagnosis and the like.

In the particle measuring method according to this aspect, the step (S14) of labeling the target polypeptide of the particle and/or other target nucleic acid different from the target nucleic acid is configured to measure the other target nucleic acid that is different from the first labeled target nucleic acid in step (S2) of labeling another target nucleic acid different from the target nucleic acid, and measuring the target nucleic acid and the labeled target polypeptide and/or other target nucleic acid.

According to the particle measuring method of this aspect, labeling and amplification can be performed simultaneously on two different target nucleic acids for one cell. Hence, the presence of an abnormality of each target nucleic acid can be examined. By associating these pieces of information complementarily, it is possible to obtain effective information for pathological diagnosis and the like.

A second aspect of the present invention relates to a sample processing method. A sample processing method according to this aspect includes a step of preparing a mixed solution containing particles and a labeled probe that binds to a target nucleic acid in the particles, and which substantially does not contain a protease, and a step of amplifying a target nucleic acid in the particle (S13).

In the sample processing method according to this aspect, preparation of the mixed solution is carried out in a state substantially free of protease. This means that the protease is not added to the mixed solution, or the protease is added to the mixed solution, but the effect of the protease is low. Usually, the amplification of the target nucleic acid in the particle is performed after the protease treatment, but in this embodiment the protease treatment is unnecessary. Hence, although treatment is usually performed to deactivate the protease during the protease treatment applied to the mixed solution, such treatment is unnecessary. Therefore, labor involved in amplifying the target nucleic acid is reduced, and amplification of the target nucleic acid proceeds efficiently. This labor reduction also contributes to cost reduction since a reagent for deactivating protease and protease is unnecessary.

The polypeptides on the surface of the particle also are not completely decomposed since the mixed solution is substantially free of protease. Hence, for example, after amplification of the target nucleic acid with respect to the particle, the target polypeptide among the polypeptides on the surface of the particle can be labeled, and the presence or absence of abnormality of the target polypeptide can be examined. In this way more tests can be performed on the same particle.

In the sample processing method according to this aspect, the mixed solution is further configured to include a DNA polymerase, and may be prepared to also include a primer. In this way a reagent necessary for amplification of the target nucleic acid is added to the mixed solution, and amplification of the target nucleic acid in the particle can proceed appropriately.

In the sample processing method according to this aspect, a step of preparing a mixed solution may be performed after the temperature of the liquid containing particles is set to 25° C. or more and 95° C. or less (S12). In this way the amplification reaction of the target nucleic acid proceeds smoothly as in the first embodiment. Protease and a reagent for deactivating protease become unnecessary since protease treatment is not required for the amplification reaction of the target nucleic acid, thus contributing to cost reduction.

In the sample processing method according to this aspect, a step of preparing a mixed solution may be performed after the temperature of the liquid containing particles is set to 25° C. or more and 75° C. or less (S12). In this way the amplification reaction of the target nucleic acid proceeds more smoothly, as in the first embodiment.

In the sample processing method according to this aspect, a step (S2) of measuring the labeled target nucleic acid may be configured to be performed after the step (S13) of labeling and amplifying the target nucleic acid.

Methods for measuring whether amplification of the target nucleic acid was properly carried out include, for example, methods of flowing a measurement sample through a flow cell irradiated with light from a light source and imaging the light given off from the flowing liquid which contains a labeled target nucleic acid and labeled target polypeptide, and a method of imaging with a fluorescence microscope. Whether amplification of the target nucleic acid has been carried out can be evaluated by such measurement.

In the sample processing method according to this aspect, the step (S2) of measuring the labeled target nucleic acid may be configured to include a step of capturing an image of the particle.

In this way the operator can visually confirm the amplification of the target nucleic acid.

In the sample processing method according to this aspect, the step of capturing an image of the particle is obtained by applying a liquid containing the labeled target nucleic acid to the flow cell (10) and irradiating the liquid in the flow cell (10) with light.

In this way it is possible to confirm the presence or absence of amplification of the target nucleic acid for a large amount of particles. Hence, the reliability of the measurement result is improved.

In the sample processing method according to this aspect, a step of analyzing the captured image may be performed after the step (S2) of measuring the labeled target nucleic acid.

In this way the cause of particle abnormality can be accurately evaluated based on the captured image.

A third aspect of the present invention relates to a particle imaging apparatus. The particle imaging apparatus according to this aspect includes a flow cell (10) through which flow a liquid containing particles in which a target nucleic acid in the particle is labeled and amplified within the particle and a target polypeptide of the particle and/or other target nucleic acid different from the target nucleic acid are labeled, a light source for irradiating light on the flow cell (10), and an imaging unit (154) for imaging the light obtained from the particles in the liquid given off by irradiating light from the light source on the flow cell.

This makes it possible to efficiently measure whether amplification of a target nucleic acid and labeling of a target polypeptide or amplification of another target nucleic acid have been performed on the same particle as in the first embodiment.

In the particle imaging apparatus according to this aspect, the flow cell (10) may be configured so as to flow therethrough a liquid containing particles wherein a target nucleic acid in the particle to be labeled and amplified within the particle and a target polypeptide on the surface of the particle.

In this way it is possible to measure whether the cause of abnormality is nucleic acid or polypeptide for a large amount of particles. Hence, the reliability of the measurement result is improved.

In the particle imaging apparatus according to this aspect, the imaging unit may be configured to capture the fluorescence from a first labeling substance that labels a target nucleic acid, and a fluorescence from a second labeling substance that labels a target polypeptide and/or other target nucleic acid different from the target nucleic acid.

In this way it is possible to clearly distinguish between presence or absence of amplification of the target nucleic acid and presence or absence of labeling of the target polypeptide or presence or absence of amplification of another target nucleic acid for the same particle. Hence, with respect to the particles to be measured, it can be determined whether the cause of abnormality is nucleic acid, polypeptide, or both. Alternatively, whether it is both mutually different nucleic acids or one or the other of them can be measured. Hence, the reliability of the measurement result is improved.

In the particle imaging apparatus according to this aspect, the liquid may be configured to be substantially free of protease.

In this way labor is reduced since it is unnecessary to deactivate the protease relative to the liquid for labeling and amplification of a target nucleic acid and labeling of a target polypeptide. This labor reduction also contributes to cost reduction since a reagent for deactivating protease and protease is unnecessary.

In the particle imaging apparatus according to this aspect, the imaging unit (154) may be configured to be a CCD camera. If the imaging unit is a CCD (Charge-Coupled Device) camera, images of the labeled target nucleic acid and the labeled polypeptide can be clearly imaged.

In the particle imaging apparatus according to this aspect, the imaging unit (154) may be configured to be a TDI camera. If the imaging unit is a TDI (Time Delay Integration) camera, fluorescence received on the light receiving surface of the imaging unit is integrated to generate a fluorescence image and a bright field image. In this way it is possible to improve the quality of the fluorescence image and the bright field image of the cell.

The present invention provides a particle measuring method, a sample processing method, and a particle imaging apparatus capable of efficiently obtaining information effective for pathological diagnosis or the like.

BRIEF DESCRIPTION OF THE DRAWINGS

FIG. 5A to FIG. 5D are, respectively, diagrams describing a particle measuring method according to a comparative example of the embodiment; FIG. 5A is a schematic diagram illustrating the amplification of the target nucleic acid; FIG. 5B is a flowchart for describing the amplification of the target nucleic acid; FIG. 5C is a schematic diagram illustrating the labeling of the target polypeptide; FIG. 5D is a flow chart describing the labeling for the target polypeptide;

FIG. 6A is a diagram illustrating a particle measuring method according to an embodiment; FIG. 6B is a diagram showing information obtained from one particle by the particle measuring method according to the embodiment;

FIG. 8 shows a bright field image, an image of a target nucleic acid, an image of a target polypeptide, and a mixed image of a target nucleic acid and a target polypeptide obtained from measurement 1 according to verification 1;

FIG. 11 shows a bright field image, an image of a target nucleic acid, an image of a target polypeptide, a mixed image of a target nucleic acid and a target polypeptide obtained from measurement 9 according to verification 6;

FIG. 14 shows a bright field image, an image of a target nucleic acid, an image of a target polypeptide, and a mixed image of a target nucleic acid and a target polypeptide obtained from measurement 12 according to verification 9;

DETAILED DESCRIPTION OF THE PREFERRED EMBODIMENTS

Embodiment

Figure 1:
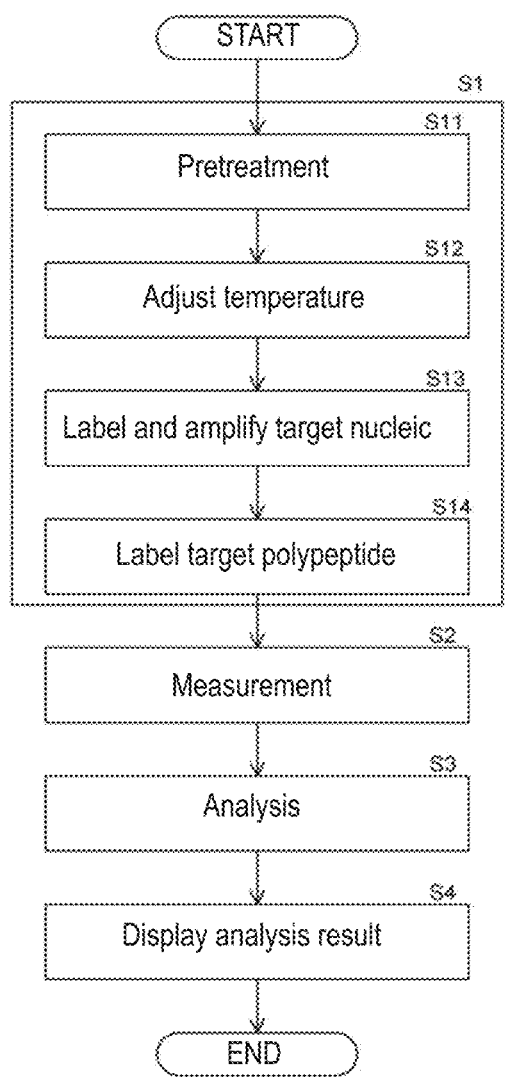
FIG. 1 is a flowchart illustrating a particle measuring method according to an embodiment.

In the particle measuring method according to an embodiment of the present invention, amplification of a target nucleic acid, binding of a target polypeptide and an antibody labeling of the polypeptide are performed on the same particle to be measured.

Here, "particles to be measured" means cells, bacteria and the like which are extracted from a specimen, have nucleic acid, and whose surface is covered with a polypeptide. The particles to be measured also may be exosomes or the like of the endoplasmic reticulum. The "specimen" mentioned above means blood specimen collected directly from a person, a piece of tissue such as skin, and the like. "Polypeptide" is a molecule in which amino acid residues are linked by peptide bonds, and includes, for example, an amino acid polymer having a relatively small molecular weight and a protein having a large molecular weight. In the particle measuring method according to the embodiment, the particles to be measured are treated with a chemical such as formalin, that is, in a state in which the particles to be measured are dispersed in a liquid, not in a state in which the particles are fixed.

Hereinafter, a case where an operator prepares a sample to be used for measurement and carries out the particle measurement method by using a device for imaging the fluorescence generated from the prepared sample will be described. All steps of the particle measurement method may be performed automatically by the apparatus.

1. Particle Measurement Method

First, a particle measuring method according to an embodiment will be described with reference to FIG. 1.

Preparation of Measurement Sample

In step S1, the operator prepares a sample for measurement, that is, a measurement sample. The preparation of this measurement sample includes the four processes of steps S11 to S14. This process will be described in detail below.

(1) Pretreatment

In step S11, the operator collects a specimen, that is, a tissue piece or the like from the subject. Particles to be measured, that is, cells, bacteria and the like are extracted from the specimen. The operator disperses the extracted particles into a liquid. The operator then mixes the liquid with a buffer solution, a reagent and the like, and performs treatment or the like by centrifugal separation.

(2) Temperature Adjustment of Liquid after Pretreatment

Next, in step S12, the operator adjusts the temperature of the liquid after the pretreatment. This process is very important in the subsequent binding of the target polypeptide to the labeled antibody. It is preferable that the temperature of the liquid after the pretreatment is adjusted within a range from 25° C. to 95° C. inclusive. The temperature is more preferably in the range of 25° C. or higher and 75° C. or lower. When the temperature of the liquid after the pretreatment is adjusted within such a range, the efficiency with which the reagent permeates into the particle to be measured increases when the polymerase and the primer are added to this liquid, and the amplification of the target nucleic acid proceeds smoothly.

(3) Amplification of the Target Nucleic Acid

Then, in step S13, the operator adds a polymerase and a primer to the pretreated liquid to prepare a mixed solution in order to amplify the target nucleic acid. In this process, the polymerase and the primer permeate efficiently into the particles to be measured due to the previous adjustment of the liquid temperature. Note that "polymerase" is, for example, DNA polymerase.

The operator then performs labeling and amplification of the target nucleic acid using a PCR apparatus. The PCR apparatus performs temperature control on the measurement sample to amplify and label the target nucleic acid. Here, amplification of the target nucleic acid may be performed after adding the first labeling substance for labeling the target nucleic acid to the mixed solution, or the first labeling substance may be added to the mixed solution after the amplification of the target nucleic acid. Note that the "first labeling substance" is a labeling substance for confirming whether amplification of the target nucleic acid has been performed, and is, for example, a labeling probe such as GAPDH_97_FAM. "First labeling substance" is used for the sake of convenience of explanation in order to distinguish from the labeling substance in the label of the target polypeptide, which will be described next.

(4) Binding Reaction Between Target Polypeptide and Labeled Antibody

Next, in step S14, the operator performs a binding reaction between the target polypeptide and the labeled antibody. Since the temperature of the liquid after the pretreatment is adjusted as described above, the shape of the polypeptide on the surface of the particle is maintained while the gap formed in the polypeptides is expanded. Therefore, the target polypeptides are labeled among the polypeptides on the surface of the particle. Therefore, according to the embodiment, both the labeling of the target nucleic acid and the labeling of the target polypeptide can be performed on the same particle.

Whether the binding reaction between the target polypeptide and the labeled antibody has been performed is confirmed with a second labeling substance different from the first labeling substance of the target nucleic acid. The second labeling substance is, for example, a labeling probe such as Alexa Fluor 647 Anti-human CD45 Antibody.

In this way preparation of the measurement sample is completed. Next, the measurement sample is subjected to measurement. In the present embodiment, a case where measurement is performed using an apparatus that images fluorescence generated from the measurement sample is described.

Measurement of Measurement Sample

In step S2, the operator acquires the image of the labeled target nucleic acid and the image of the labeled target polypeptide using an apparatus for imaging the fluorescence generated from the measurement sample. The apparatus used in step S2 is a particle imaging apparatus, for example a flow cytometer.

Figure 2:
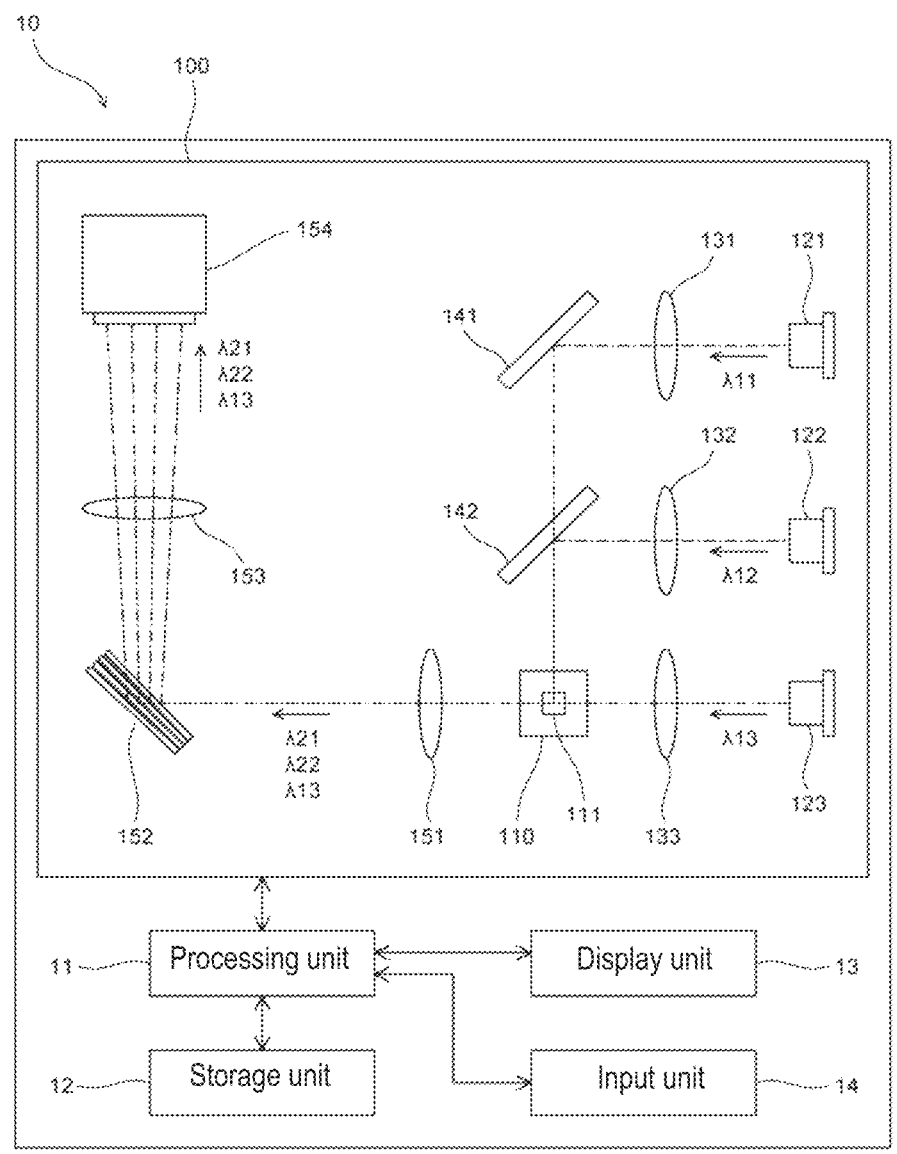
FIG. 2 is a schematic structural diagram relating to a flow cytometer to which a particle measuring method according to an embodiment is applied.

FIG. 2 is a diagram schematically showing a configuration of a flow cytometer. The flow cytometer 10 includes an imaging unit 100, a processing unit 11, a storage unit 12, a display unit 13, and an input unit 14. The imaging unit 100 includes a flow cell 110, light sources 121 to 123, condenser lenses 131 to 133, a mirror 141, a dichroic mirror 142, a condenser lens 151, an optical unit 152, a condenser lens 153, and an imaging unit 154.

As described above, in step S1, the prepared measurement sample is flowed into the flow channel 111 of the flow cell 110 provided in the flow cytometer 10. The particles contained in the measurement sample are imaged by the imaging unit 100.

The light sources 121 to 123 irradiate light on the measurement sample flowing through the flow cell 110. The light sources 121 to 123 are configured by, for example, a semiconductor laser or an argon laser. The light emitted from the light sources 121 to 123 are laser light having different wavelengths $\lambda 11$ to $\lambda 13$, respectively. The condensing lenses 131 to 133 collect the light emitted from the light sources 121 to 123, respectively. The mirror 141 reflects the light of the wavelength $\lambda 11$. The dichroic mirror 142 transmits light of wavelength $\lambda 11$ and reflects light of wavelength $\lambda 12$. In this way the light having wavelengths $\lambda 11$ to $\lambda 13$ is irradiated onto the measurement sample flowing through the flow channel 111 of the flow cell 110.

When the measurement sample is irradiated with light of the wavelengths $\lambda 11$ and $\lambda 12$, fluorescence is generated from the fluorescent stains which stain the particles. Specifically, fluorescence having a wavelength $\lambda 21$ is generated when a fluorescent stain that labels a target nucleic acid, that is, a first labeling substance, is irradiated with light having a wavelength $\lambda 11$. Fluorescence having a wavelength $\lambda 22$ is generated when a fluorescent stain that labels a target polypeptide, that is, a second labeling substance is irradiated with light having a wavelength $\lambda 12$. When light of wavelength $\lambda 13$ is irradiated on the measurement sample, this light is transmitted through the cell. The light having the wavelength $\lambda 13$ transmitted through the cell is used for generating a bright field image. Note that the wavelengths $\lambda 21$, $\lambda 22$, and $\lambda 13$ are different from each other.

The condenser lens 151 collects the fluorescence of the wavelengths $\lambda 21$ and $\lambda 22$ generated from the measurement sample flowing through the flow channel 111 of the flow cell 110 and the light of the wavelength $\lambda 13$ transmitted through the measurement sample flowing through the flow channel 111 of the flow cell 110. The optical unit 152 has a configuration in which three dichroic mirrors are combined. The three dichroic mirrors of the optical unit 152 reflect the fluorescence of the wavelengths $\lambda 21$, $\lambda 22$, and the light of the wavelength $\lambda 13$ at slightly different angles from each other and separates them on the light receiving surface of the imaging unit 154. The condenser lens 153 collects the fluorescence of the wavelengths $\lambda 21$, $\lambda 22$ and the light of the wavelength $\lambda 13$.

The imaging unit 154 is configured by, for example, a CCD (Charge-Coupled Device) camera or a CMOS (Complementary Metal-Oxide Semiconductor) camera. With a CCD camera, images of the labeled target nucleic acid and the labeled polypeptide can be clearly imaged. The imaging unit 154 also is preferably configured by a TDI (Time Delay Integration) camera. The TDI camera integrates the fluorescence received on the light receiving surface to generate a fluorescence image and a bright field image. In this way it is possible to improve the quality of the fluorescence image and the bright field image of the cell. The imaging unit 154 images the fluorescence of the wavelengths $\lambda 21$ and $\lambda 22$ and the light of the wavelength $\lambda 13$, and outputs fluorescence images corresponding to the fluorescence of the wavelengths $\lambda 21$ and $\lambda 22$, and a bright field image corresponding to the light of the wavelength $\lambda 13$ as imaging signals.

The processing unit 11 is configured by a CPU. The processing unit 11 is not limited to this configuration, and may be configured by a CPU and a microcomputer. The processing unit 11 performs various processes based on a program stored in the storage unit 12. The processing unit 11 is connected to the imaging unit 100, the storage unit 12, the display unit 13, and the input unit 14, receives signals from each unit, and controls each unit. The storage unit 12 is configured by a RAM, a ROM, a hard disk and the like. The display unit 13 is configured by a liquid crystal display, a plasma display, a CRT (Cathode Ray Tube) display or the like. The input unit 14 is configured by, for example, a mouse, a keyboard or the like.

The processing unit 11 causes the storage unit 12 to store the fluorescence images and the bright-field image captured by the imaging unit 154. When the operator inputs an image display instruction via the input unit 14, the processing unit 11 displays the measurement result screen 200 including the fluorescence images and the bright field image on the display unit 13.

Figure 3:
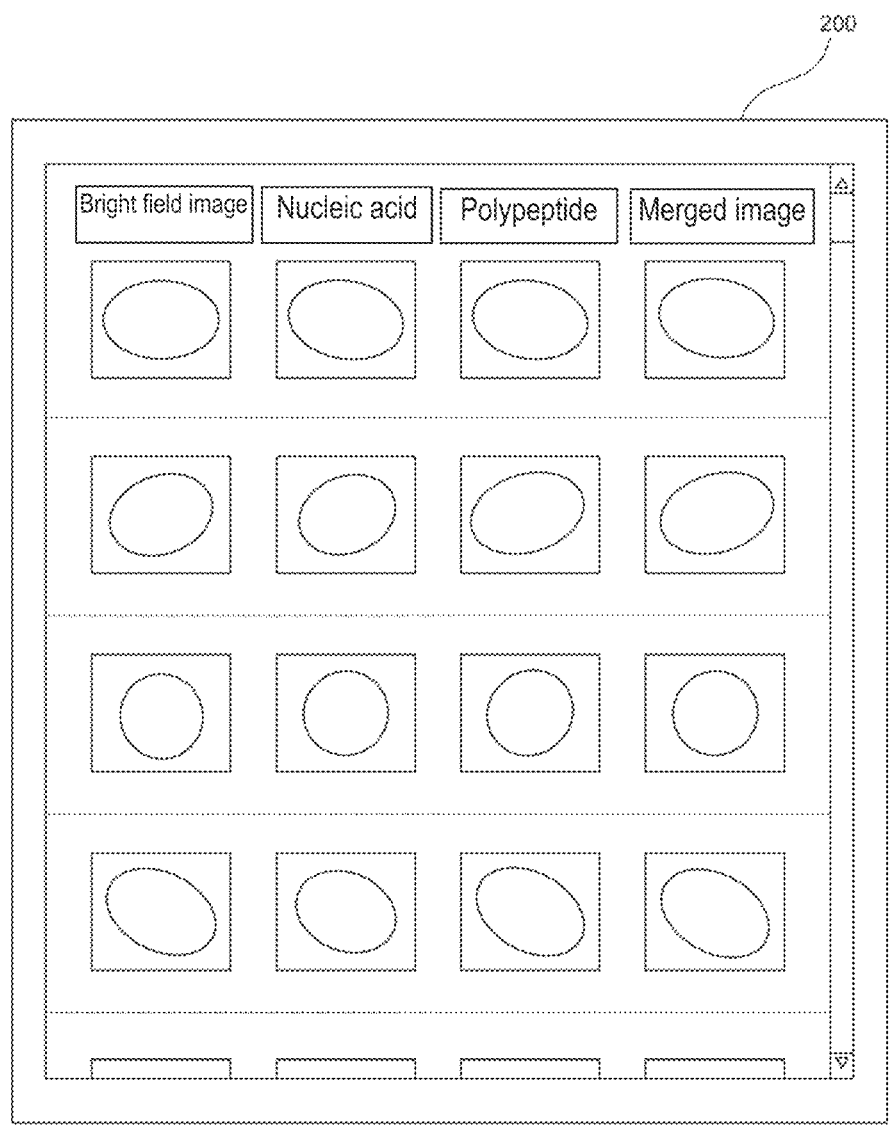
FIG. 3 is a diagram showing a display unit for displaying a bright field image, a fluorescence image based on a target nucleic acid, a fluorescence image based on a target polypeptide, and a merged image.

As shown in FIG. 3, the measurement result screen 200 displays a bright field image, a fluorescence image based on the target nucleic acid, a fluorescence image based on the target polypeptide, and a merged image (mixed image). The merged image is a fluorescence image obtained by merging a fluorescence image based on the target nucleic acid and a fluorescence image based on the target polypeptide. The measurement result of the measurement sample measured by the flow cytometer 10 is displayed in this way.

Note that, in addition to the flow cytometer, measurement of the measurement sample also may include acquisition of an image by, for example, a fluorescence microscope.

Analysis

In step S3, the processing unit 11 analyzes predetermined items based on the image of the labeled target nucleic acid and the image of the labeled target polypeptide acquired in step S2. For example, in the case where the measurement sample is measured by the flow cytometer 10, the number of target nucleic acids and target polypeptides is counted from the measurement result displayed on the measurement result screen 200 shown in FIG. 3, and cells, bacteria and the like are evaluated as normal or abnormal. From the perspective of whether the target nucleic acid or the target polypeptide clearly appears in the image, it also is possible to evaluate whether the cause of abnormality of a particle, that is, cell, bacterium and the like is a nucleic acid, a polypeptide, or both.

Display of Analysis Result

Figure 4:
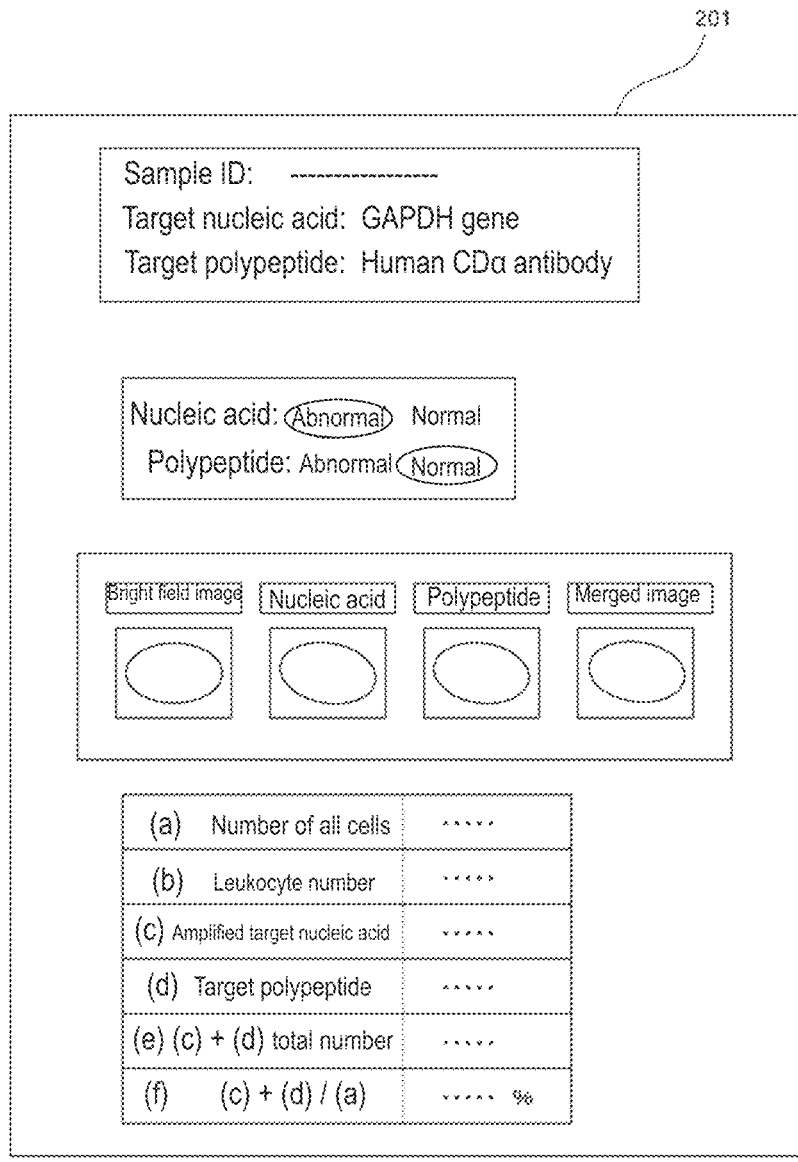
FIG. 4 is a view showing an example of a screen displaying an analysis result based on a measurement result of a measurement sample.

In step S4, the processing unit 11 causes the display unit 13 to display the analysis result screen 201 as a result of analysis in step S3, as shown in FIG. 4. FIG. 4 shows, as an example of a display in which the measurement object is white blood cells, the target nucleic acid is the GAPDH gene, and the target polypeptide is human CD$\alpha$ antigen. In the "Analysis Result" column, the presence or absence of abnormality of nucleic acids and polypeptides is displayed. In FIG. 4, for example, there is an abnormality in the nucleic acid, whereas the polypeptide is normal. The measurement result obtained in step S2 also may be displayed on the analysis result screen 201. Scattergrams and histograms also may be created.

Displaying the analysis result in this way makes it possible, for example, for a doctor or the like to examine the abnormality of the nucleic acid and the polypeptide for diagnosing the disease, and for use in determining the treatment policy.

2. Comparison of Particle Measuring Method of Comparative Example and Particle Measuring Method of Embodiment Since the amplification of the target nucleic acid and the labeling of the target polypeptide are performed on the same particle in the particle measuring method according to the embodiment, the particle measuring method according to the embodiment is significantly different from the conventional particle measuring method. Hereinafter, the conventional particle measuring method is used as a comparative example and compared with the particle measuring method according to the embodiment of the present invention. Hereinafter, with reference to FIGS. 5A to 5D, consideration is given to a case in which nucleic acid amplification is carried out in order to investigate the cause of disease by applying the particle measuring method according to the comparative example.

Particle Measuring Method According to Comparative Example

FIG. 5A and FIG. 5B are respectively a schematic diagram and a flow chart showing a procedure of amplification of a target nucleic acid in a comparative example.

In the comparative example, particles to be measured, that is, cells and bacteria collected from a subject are treated with a drug such as formalin from the viewpoint of preservation. This condition is a so-called "fixed cell state" and it is impossible to infiltrate a reagent containing DNA polymerase and a primer into a cell in this state. Therefore, in the comparative example, as shown in FIG. 5A, a treatment for degrading the polypeptide, that is, a protease treatment is required when amplifying the target nucleic acid.

As shown in FIG. 5B, a protease process is performed in step S101. In the comparative example shown in FIG. 5A, a reagent for amplifying the target nucleic acid can permeate into the cell since the polypeptide is decomposed by the protease treatment. Then, in step S102 amplification of the target nucleic acid is performed. Thereafter, the operator acquires an image of the target nucleic acid using, for example, a fluorescence microscope or the like.

If amplification of the target nucleic acid in the cell is not confirmed in the acquired image of the target nucleic acid, it is understood that the cause of the disease is not found in the nucleic acid. In this case, a possible cause is the occurrence of abnormality in a polypeptide.

FIGS. 5C and 5D are a schematic diagram and a flow chart respectively showing a procedure of labeling a polypeptide in a comparative example.

As shown in FIG. 5D, the target polypeptide is labeled by performing a binding reaction between the target polypeptide and the labeled antibody in step S103. Here, the polypeptide used for amplification of the target nucleic acid is degraded by protease treatment. Therefore, the binding reaction between the target polypeptide and the labeled antibody cannot be performed on the cells used for the amplification of the target nucleic acid. Therefore, the operator separately prepares samples including other cells collected from the same subject, and then performs a binding reaction between the target polypeptide and the labeled antibody. Also in this case, the operator acquires an image of the target polypeptide using, for example, a fluorescence microscope or the like.

As described above, in the comparative example, the operator needs to perform amplification of the target nucleic acid and binding reaction between the target polypeptide and the labeled antibody separately, which is troublesome and complicated. The above processing also is performed in a state where cells are placed on a slide glass. Therefore, a burden is imposed on the operator when it is desired to amplify a target nucleic acid to many particles, that is, cells.

In the comparative example, the information gained from one particle is either the presence or absence of an abnormal nucleic acid or the presence or absence of a target polypeptide. In other words, only one piece of information can be obtained from one particle. For this reason nucleic acid and polypeptide information cannot be complementarily evaluated for one particle.

Differences Between Particle Measuring Method of Comparative Example and Particle Measuring Method of Embodiment Next, the point that the particle measuring method according to the embodiment of the present invention is different from the particle measuring method according to the comparative example will be described.

In the embodiment, amplification of the target nucleic acid and labeling of the target polypeptide are performed on the same particle. The binding reaction between the target polypeptide and the labeled antibody in the embodiment can be carried out because the polypeptide on the surface of the particle is not completely decomposed.

As a factor enabling the above, in the embodiment the particles to be measured, that is, cells, are in a state of dispersion in a liquid. That is, unlike the comparative example, the particles are not in a fixed state in the embodiment. Therefore, although it is necessary to apply a certain degree of impact to the polypeptide on the surface of the particle when a reagent containing a polymerase and a primer penetrates into the particle, an impact as strong as that required in the comparative example is unnecessary.

Therefore, in the particle measuring method according to the embodiment, the temperature of the liquid after the pretreatment is adjusted as shown in FIG. 6A in order to permeate the reagent fully into the particle. The temperature adjustment shown in FIG. 6A corresponds to the temperature adjustment (S12) of the liquid after the pretreatment in step S1 of FIG. 1. In this way the polypeptide on the surface of the particle is not completely decomposed, and its shape is maintained while the gap widens. Through this expanding gap, a reagent including a polymerase and a primer penetrates into the inside of the particle. In this way amplification of the target nucleic acid is carried out in the particle even in a state substantially not containing the protease. The amplification of the target nucleic acid shown in FIG. 6A corresponds to the process of labeling and amplifying the target nucleic acid in step S1 of FIG. 1 (S13).

Note that although a state of adding a labeled probe for labeling the target nucleic acid before amplification of the target nucleic acid is shown in FIG. 6A, this addition may be performed after amplification of the target nucleic acid.

As used herein, the term "substantially free from protease" does not mean only when no protease is added to the mixed solution, "substantially free from protease" also means a case in which protease is added to the mixed solution but the amount thereof is extremely small and the effect of the protease is not exerted.

Therefore, in step S1 of FIG. 1, amplification of the target nucleic acid is performed and then the binding reaction between the target polypeptide and the labeled antibody with respect to the polypeptide on the surface of the undegraded particle also can be performed on the same particle.

As described above, amplification of the target nucleic acid and labeling of the target polypeptide can be performed on one particle, that is, one cell, bacterium or the like in the particle measuring method according to the embodiment.

Therefore, it is possible to efficiently amplify the target nucleic acid and label the target polypeptide.

Effects of Particle Measuring Method of Embodiment

The particles of the embodiment, that is, cells, bacteria and the like are in a state of dispersion in a liquid. Therefore, it is unnecessary for the operator to put the particles on a slide glass or the like as when, for example, particles are fixed with a chemical such as formalin as in the comparative example. Hence, with the particle measuring method according to the embodiment, the operator can measure the target nucleic acid at once relative to a large amount of cells using a flow cytometer.

There also is no need to prepare cells for amplification of the target nucleic acid and labeling of the target polypeptide. This, for example, eliminates the need to collect specimens or tissue pieces many times from diseased patients, which leads to reduction of stress of the patient.

In the embodiment, the polymerase and the primer also penetrate into the particle substantially without influence of the protease. Therefore, it is unnecessary to perform a process to inactivate the protease. Hence, reagent can be saved.

As described above, in the comparative example the information obtained from one particle is the presence or absence of abnormality of the nucleic acid, or presence or absence of abnormality of the polypeptide. In other words, only one piece of information can be obtained from one particle. In contrast, by matching the presence or absence of abnormality of nucleic acid and presence or absence of abnormality of polypeptide, information matching one of the four combinations can be obtained from one particle n the particle measuring method according to the embodiment, as shown in FIG. 6B. Since information of both nucleic acids and polypeptides can be obtained at once and also in large amounts, more reliable information can be obtained. Associating these pieces of information complementarily makes it possible to evaluate the particles with high accuracy. As a result, it is possible to propose appropriate dosing and treatment policies for patients.

Information on the target nucleic acid and information on the polypeptide on the surface of the particle also are obtained from a single particle, so that this method can be expected to become a new biomarker for pathological diagnosis. This is because, for example, when acquiring from nucleic acid information indicating that mutation has occurred in a nucleic acid and the cell has become cancerous, and if information on the expression of PD-L1 (programmed cell death-1 ligand-1) can be obtained on the surface of the carcinoma cells, it becomes possible to select as a therapeutic agent niborumar which is an anti-PD-1 antibody drug as a cancer remedy.

When acquiring from the nucleic acid information that mutation has occurred in a blood cell or exosome nucleic acid and the cell is carcinogenic, it is possible to identify from which organ the cell or exosome is derived by obtaining information on the surface antigen of the cell or exosome. This helps to determine which organ has a tumor.

Validation of Particle Measuring Method of Embodiment

Next, in order to verify the conditions for optimally performing amplification of the target nucleic acid and labeling of the target polypeptide of the same particle, namely cells, bacteria and the like by the particle measuring method according to the embodiment of the present invention, the inventors conducted verifications 1-8. First, the procedure for the preparation of measurement samples to be subjected to verifications 1 to 8 will be described.

Preparation of Measurement Sample (A) Pretreatment

White blood cells were used for the particles to be measured. The target nucleic acid was the GAPDH gene, and the target polypeptide was the human CD45 antigen.

(A-1) Leukocytes collected in an appropriate amount from a subject were dispersed in a liquid to make the total amount 200 JAL. This was placed in a predetermined tube.

(A-2) 1 mL of hemolytic agent was added to the tube.

(A-3) Ice-cooled for 15 minutes.

(A-4) The tube was centrifuged at 400 rpm for 10 minutes under an environment of 4° C.

(A-5) The supernatant was removed.

(A-6) 400 µL of a hemolytic agent was added to the tube, and the content in the tube was washed.

(A-7) The tube was centrifuged at 400 rpm for 10 minutes under an environment of 4° C.

(A-8) supernatant was removed.

(A-9) 180 µL of PBS was placed in the tube, and the contents were suspended.

(A-10) The content was adjusted to a predetermined temperature and held for a predetermined time.

(A-11) The tube was centrifuged at 400 rpm for 10 minutes under an environment of 4° C.

(A-12) Supernatant was removed.

(B) Amplification of Target Nucleic Acid (B-1) In order to amplify the target nucleic acid, a reagent was added to the tube. The composition of the reagent was as follows:

3' terminal side primer: GAPDH-97_F
5' end side primer: GAPDH-97_R
DNA polymerase: Taqman (registered trademark) Gene Expression Master Mix
Labeled probe of target nucleic acid: GAPDH-97_FAM
Distilled water (B-2) Concentration and amount of each composition contained in the reagent were as follows. Note that in the following, "before use" means the product state or the storage state. "Final concentration" is the concentration when prepared as a reagent.

3' end side primer: 0.5 µL was added to the tube. The concentration before use was 10.0 µM and the final concentration was 0.2 µM.

5' end primer: 0.5 µL was added to the tube. The concentration before use was 10.0 µM and the final concentration was 0.2 µM.

Taqman (registered trademark) Gene Expression Master Mix: 2× concentrated as a product, but diluted to 1× for use. To the tube, 12.5 µL of Taqman (registered trademark) Gene Expression Master Mix diluted 1 time was added.

GAPDH-97_FAM: 0.5 µL was added to the tube. The concentration before use was 10.0 µM and the final concentration was 0.2 µM.

Distilled water: 11 µL was added to the tube.

Reagents were prepared as described above. The total amount was 25.0 µL.

(B-3) After the addition of the reagent as described above, the tube was set in a PCR apparatus, and the amplification reaction of the target nucleic acid was carried out. The amplification reaction of the target nucleic acid was carried out at 50° C. for 2 minutes and then at 95° C. for 10 minutes, followed by two stages of 40 cycles of 95° C. for 15 seconds as the first stage and 60 seconds at 60° C. as the second stage.

(C) Labeling of Target Polypeptide

Following amplification of the target nucleic acid, the binding reaction between the target polypeptide and the labeled antibody was carried out. The procedure is shown below.

(C-1) 75 μL of PBS was placed in the tube, and the measurement sample was suspended.

(C-2) 5 μL of anti-CD45 antibody was added to the tube. In addition, Alexa Fluor 647 anti-human CD45 Antibody (BioLegend) was used as a labeling probe for labeling the binding reaction between the target polypeptide and the labeled antibody.

(C-3) The binding reaction between the target polypeptide and the labeled antibody was carried out for 60 minutes under an environment of 4° C.

The following verification was carried out using the measurement sample prepared by the above procedure.

Verification 1: Relationship Between Efficiency of Amplification of Target Nucleic Acid and Temperature Adjustment of Liquid After Pretreatment In verification 1, the efficiency of amplification of the target nucleic acid was measured, and it was verified whether amplification of the target nucleic acid was carried out with the measurement sample prepared by the above procedure. The relation with the temperature adjustment of the contents, that is, the liquid, after the pretreatment was also verified. Specifically, whether there was a change in the efficiency of amplification of the target nucleic acid when the temperature was different in the procedure (A-10) for preparing the measurement sample was verified.

In procedure (A-10), the temperature of the contents was set to 1: 25° C., 2: 50° C., 3: 75° C., 4: 95° C., 5: 100° C., and the holding time at all temperatures was 2 minutes. Note that, except for the condition of temperature, conditions were the same.

Figure 7:
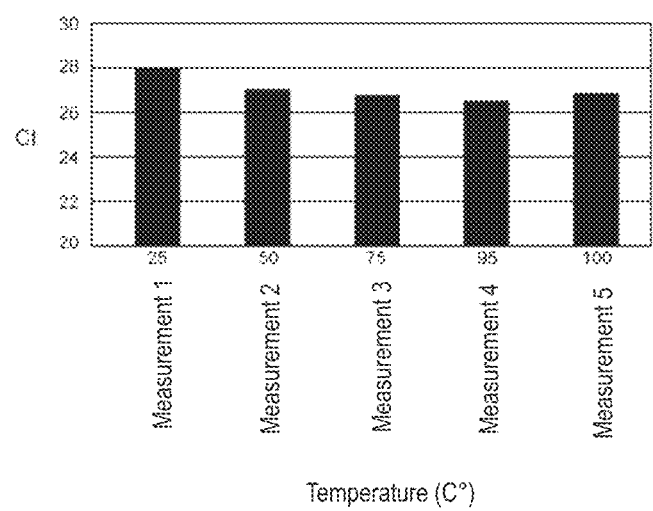
FIG. 7 is a graph showing the results of measurements 1 to 5 according to verification 1.

The verification results are shown in the graph of FIG. 7. The Ct value shown in FIG. 7 is an index showing the efficiency of amplification of the target nucleic acid; the lower the Ct value, the better the amplification efficiency of the target nucleic acid. As shown in the graph of FIG. 7, the Ct values were different depending on each temperature. Hence, it was found that the temperature adjustment of the liquid after the pretreatment influenced the efficiency of amplification of the target nucleic acid. Since the Ct value is the lowest in the case of measurement 4 (95° C.), the efficiency of amplification of the target nucleic acid is the best when the liquid after the pretreatment is adjusted to 95° C. in the procedure (A-10).

Conclusion of Verification 1

Amplification of the target nucleic acid is not affected even when the target polypeptide is labeled in the measurement sample after amplification of the target nucleic acid. The temperature at the time of temperature adjustment of the liquid after pretreatment influences the efficiency of amplification of the target nucleic acid.

When the temperature of the liquid after the pretreatment is adjusted to 95° C. and the holding time is set to 2 minutes, the efficiency of amplification of the target nucleic acid is good.

Verification 2: Amplification of Target Nucleic Acid and Labeling of Target Polypeptide In verification 1, it was found that in the procedure (A-10) the efficiency of the amplification of the target nucleic acid was improved when the temperature of the liquid after the pretreatment was adjusted to 95° C. and the holding time was 2 minutes (measurement 4). However, verification 1 has not been verified as to whether labeling of the target polypeptide was appropriately performed. Therefore, for each of the conditions 1 to 5 of verification 1, it was verified whether amplification of target nucleic acid and labeling of target polypeptide were properly performed.

In verification 2, the ratio of the total of the number of cells where amplification of the target nucleic acid was performed and the number of cells which had the target polypeptide labeled was divided by all cells was calculated. That is, since this ratio is the ratio at which both the amplification of the target nucleic acid and the labeling of the target polypeptide are performed, it can be determined that the higher the value, the more efficiently the reactions of both were performed. The results are shown in Table 1.

TABLE 1

| | (a) Temperature, reaction time | (b) Number of total cells | (c) Number of leukocytes | (d) Number of cells with amplified target nucleic acid and labeled target polypeptide | (e) (d)/(c) (%) |
|---|---|---|---|---|---|
| Measurement 1 | 25° C., 2 min | 6123 | 3135 | 1368 | 43.6 |
| Measurement 2 | 50° C., 2 min | 18279 | 7258 | 2046 | 28.2 |
| Measurement 3 | 75° C., 2 min | 26829 | 9444 | 2125 | 22.5 |
| Measurement 4 | 95° C., 2 min | 44154 | 11295 | 1891 | 16.7 |
| Measurement 5 | 100° C., 2 min | 6508 | 2152 | 319 | 14.8 |

The (b) total cell number and (c) white blood cell count in Table 1 were measured with a general purpose flow cytometer. (D) The amplification of the target nucleic acid and the number of cells labeled with the target polypeptide were calculated from the images taken by the flow cytometer. In the calculation of (d) in Table 1, it was determined that the target nucleic acid was amplified and the target polypeptide was labeled when the fluorescence intensity in the fluorescence image based on the target nucleic acid is a predetermined threshold value or higher and the fluorescence intensity in the fluorescence image based on the target polypeptide is a predetermined threshold value or higher. Then, the number of cells for which it was determined that the target nucleic acid was amplified and the target polypeptide was labeled were taken as values in (d) in Table 1.

In verification 1, as shown in the graph of FIG. 7, the efficiency of amplification of the target nucleic acid was the best in the case of measurement 4. However, according to the results of Table 1, in the case of measurement 4, the ratio (e) of the cells in which amplification of the target nucleic acid and labeling of the target polypeptide was performed was as low as 16.7%. In contrast, the ratio (e) of measurement 1 was the highest, 43.6%, and the ratio (e) of measurement 2 and measurement 3 were 28.2% and 22.5%, respectively. From this result, it was found that in the procedure (A-10), the ratio (e) decreases as the temperature of the liquid after the pretreatment is adjusted to a higher temperature. In particular, the ratio (e) at 100° C. of verification 5 was as low as 14.8%.

From the results of verification 2, it was found that both amplification of the target nucleic acid and labeling of the target polypeptide can be performed efficiently when performed in the range of the temperature of the liquid after pretreatment in the procedure (A-10) in the range of 25° C. to 95° C. in the particle measuring method according to the embodiment.

Here, in the case of measurement 4, the ratio (e) was as low as 16.7%, but at least amplification of the target nucleic acid is performed satisfactorily as shown in the graph of FIG. 7 which is the result of verification 1. Therefore, in the case of measurement 4, it can be determined that amplification of the target nucleic acid and labeling of the target polypeptide were both performed on the same cell.

Note that in the case of measurement 5 when the temperature of the liquid after pretreatment was adjusted to a high temperature, it is conceivable that the cells themselves were affected such that the number of cells contained in the sample decreased and the number of cells to be measured decreased before amplification of the target nucleic acid. Hence, a large amount of cells is considered necessary when the temperature is raised to a high temperature in procedure (A-10) in order to achieve a state in which the amplification efficiency of the target nucleic acid is good and the ratio of amplification of the target nucleic acid and the number of cells labeled with the target polypeptide.

As described above, the amplification of the target nucleic acid (d) in Table 1 and the number of cells labeled with the target polypeptide were calculated from images captured with a flow cytometer. Specifically, such an image is shown in FIG. 8. Each image in FIG. 8 is an image obtained by imaging particles of measurement 1, and include in order from the left side, a bright field image, an image of a target nucleic acid, an image of a target polypeptide, and the image on the far right side is a merged image of the target nucleic acid amplification image and the image of the target polypeptide. In this way, it is possible to appropriately acquire the image of the target nucleic acid and the image of the target polypeptide imaged by the flow cytometer by performing the procedure of the measurement sample according to the embodiment.

Conclusions of Verification 1

The amplification of the target nucleic acid and labeling of the target polypeptide with respect to the same cell can be carried out satisfactorily by setting the temperature holding time to 2 minutes at the time of adjusting the temperature of the liquid after the pretreatment, and setting the temperature within the range of 25° C. to 95° C.

Efficiency is better especially when temperature is set in the range of 25° C. or more and 75° C. or less.

Verification 3: Efficiency of Amplification of Target Nucleic Acid and Temperature Adjustment of Liquid after Pretreatment In verification 1, it was found that the efficiency of amplification of the target nucleic acid was best when the temperature of the liquid after the pretreatment was adjusted at 95° C. Here, in verification 3, the relationship between the time to adjust the temperature of the liquid after the pretreatment and the efficiency of amplification of the target nucleic acid was verified.

In procedure (A-10) the temperature of the liquid after pretreatment was set at 95° C., and the holding time was set at 1 minute in measurement 6, and set at 10 minutes in measurement 7. Measurement 1 in which the temperature of the liquid after pretreatment was adjusted to 25° C. in the temperature adjustment of procedure (A-10), the percentage of cells in which the target nucleic acid was amplified and the target polypeptide was labeled was good in the verification 2. Measurement 8 was performed when the temperature of the liquid after the pretreatment was adjusted to 25° C. and the holding time was set to 0 minutes; the relationship between the time of adjusting the temperature of the liquid after the pretreatment and the efficiency of amplification of the target nucleic acid was examined in measurement 8. The Ct values of measurements 6 to 8 are shown in FIG. 9.

Figure 9:
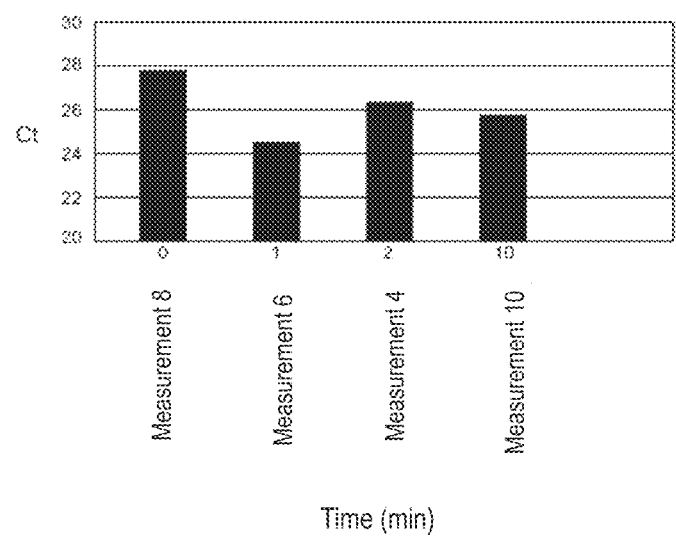
FIG. 9 is a graph showing the results of measurements 4, and 6 to 8 according to verification 2.

As a result, the Ct value of measurement 6 was lower than the Ct value of measurement 4 as shown in FIG. 9. Hence, when adjusting the temperature of the liquid after pretreatment to 95° C. in procedure (A-10), it was found that amplification of the target nucleic acid is performed efficiently if the holding time is 1 minute.

In measurement 8, although the Ct value was the highest, the efficiency of amplification of the target nucleic acid was inferior to that of measurements 6 and 7, yet was almost the same as that of measurement 1 as shown in the graph of FIG. 7 of verification 1. Therefore, under the conditions of measurement 8, which are similar those of measurement 1, it was expected that the ratio of amplification of the target nucleic acid and labeling of the target polypeptide was high.

Conclusions of Verification 3

When the temperature of the liquid after the pretreatment is adjusted to 95° C. and the holding time is 1 minute, the amplification efficiency of the target nucleic acid is good.

Verification 4: Amplification of Target Nucleic Acid and Labeling of Target Polypeptide Next, similar to verification 2, whether amplification of the target nucleic acid and labeling of the target polypeptide occurred when carried out under the conditions of measurement 6 to 8 was verified. The number of cells with amplified target nucleic acid plus cells with labeled target polypeptide was divided by the total number of cells to calculate the ratio. The results are shown in Table 2.

TABLE 2

| | (a) Temperature, reaction time | (b) Number of total cells | (c) Number of leukocytes | (d) Number of cells with amplified target nucleic acid and labeled target polypeptide | (e) (d)/(c) (%) |
|---|---|---|---|---|---|
| Measurement 6 | 95° C., 1 min | 35062 | 10805 | 1563 | 14.5 |
| Measurement 7 | 95° C., 10 min | 8248 | 3024 | 487 | 16.1 |
| Measurement 8 | 25° C., 0 min | 14565 | 7177 | 3265 | 45.5 |

From the results in Table 2, 45.5% of the measurement 8 was the highest in the ratio (e) of the amplification of the target nucleic acid and the labeling of the target polypeptide. This agrees with the result expected from the result of verification 3. In contrast, the ratio (e) of measurement 6 and measurement 7 was 14.5% and 16.1%. Verification 4 also showed a decrease in the ratio as the temperature of the liquid after pretreatment was adjusted to higher temperature, as in verification 2. The cause is considered to be the same as verification 2.

Conclusions of Verification 4

When the temperature of the liquid after the pretreatment is adjusted to 95° C. and the holding time is set to 1 minute and 10 minutes, respectively, amplification of the target nucleic acid and labeling of the target polypeptide are performed on the same cell.

Even when the temperature of the liquid after the pretreatment is adjusted to 25° C., amplification of the target nucleic acid and labeling of the target polypeptide are performed on the same cell.

Summary of Verifications 1 to 4

From the results of the measurements 1 to 8 in verifications 1 to 4, it is understood that the amplification number of the target nucleic acid and the labeling of the target polypeptide are efficiently carried out in procedure (A-10) of the particle measuring method according to the embodiment, that is, the temperature adjustment of the liquid after the pretreatment is adjusted to a range of 25° C. to 95° C. It also was found that it is more efficiently performed when the temperature was in the range of 25° C. or more and 75° C. or less.

Verification 5: Relationship Between Labeling of Target Polypeptide and Adjustment of Temperature In verifications 1 to 4, it was found that the efficiency of amplification of the target nucleic acid is influenced by the temperature in procedure (A-10) of the measurement sample. Next, in the procedure (A-10) of in verification 5, labeling of the target polypeptide was performed instead of amplification of the target nucleic acid in the temperature-adjusted pretreatment liquid, and whether the adjustment of the temperature affected the labeling of the target polypeptide was verified.

In measurement 4 (when the temperature was adjusted at 95° C. for 2 minutes), after the temperature was adjusted in the procedure (A-10), the target polypeptide was labeled, and an image of the target polypeptide was acquired by a flow cytometer. The image is shown in FIG. 10.

Figure 10:
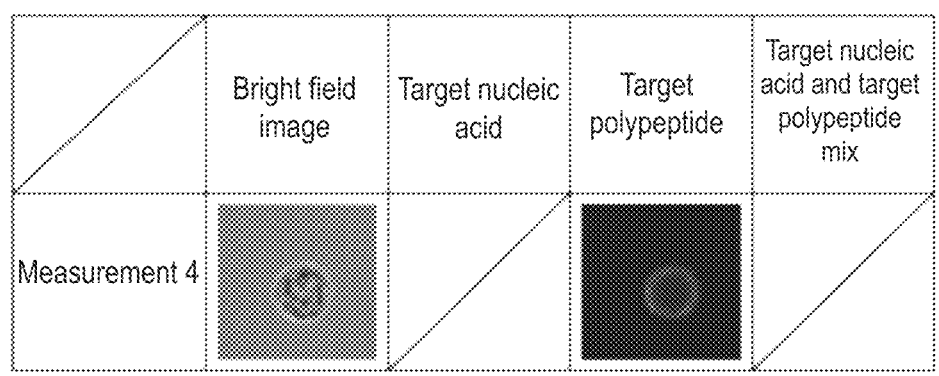
FIG. 10 shows a bright field image, an image of a target nucleic acid, an image of a target polypeptide, and a mixed image of a target nucleic acid and a target polypeptide obtained from measurement 4 according to verification 5.

The images in FIG. 10 include, in order from the left side like the image shown in FIG. 8, a bright field image, an image of a target nucleic acid, an image of a target polypeptide, and the rightmost image is a merged image of the image of amplification of the target nucleic acid and the image of the target polypeptide. As shown in FIG. 10, the target polypeptide is properly labeled with the labeled antibody in measurement 4. Hence, it was found that regulation of the temperature did not affect the labeling of the target polypeptide.

Conclusions of Verification 5

Adjusting the temperature of the liquid after pretreatment does not affect the labeling of the target polypeptide.

Verification 6: Sequence of Amplification of Target Nucleic Acid and Labeling of Target Polypeptide In verifications 1 to 4, the target nucleic acid was amplified and then the target polypeptide was labeled. In Verification 6, the accuracy of the amplification of the target nucleic acid and the labeling of the target polypeptide was verified when the target nucleic acid is amplified in reverse, that is, after labeling of the target polypeptide.

In measurement 4, following procedure (A-12) for preparing the measurement sample, procedure (C), that is, the labeling of the target polypeptide was performed, followed by procedure (B), that is, amplification of the target nucleic acid. This measurement condition was taken as measurement 9. Images of target nucleic acids and target polypeptides were then obtained with a flow cytometer. The image is shown in FIG. Image in FIG. 11 include, in order from the left side like the images shown in FIGS. 8 and 10, a bright field image, an image of a target nucleic acid, an image of a target polypeptide, and the rightmost image is a merged image of an image of the target nucleic acid and the image of the target polypeptide.

In the images other than the bright field image in FIG. 10, unevenness in color development was observed, as well as blurred outlines. The images other than the bright field image in FIG. 10 were also blurred overall, including the outline, and it were unclear images. Therefore, it was shown that both amplification of the target nucleic acid and labeling of the target polypeptide are difficult when amplifying the target nucleic acid after labeling the target polypeptide with the labeled antibody. Therefore, it has been shown that amplification of the target nucleic acid, and the ability to label the target polypeptide with good precision can be achieved by labeling the target polypeptide after amplification of the target nucleic acid as in the embodiment.

Conclusions of Verification 6

Amplification of the target nucleic acid and labeling of the target polypeptide can be performed with high accuracy by amplifying the target nucleic acid and then labeling the target polypeptide with the labeled antibody.

Validation 7: When the Measurement Target is an Exosome

In the above verifications 1 to 6, the object to be verified was white blood cells. Next, whether amplification of the target nucleic acid can be performed by the particle measuring method according to the embodiment is verified for other than white blood cells, for example, bacteria or the like.

Measurement samples were prepared using exosome which is an endoplasmic reticulum as a measurement object. However, since the target polypeptide was not labeled, only processes (A) and (B) were carried out. In the step of adjusting the temperature of process (A-10), the content of the tube was adjusted to 25° C. and held for 2 minutes. This is called measurement 10.

Figure 12:
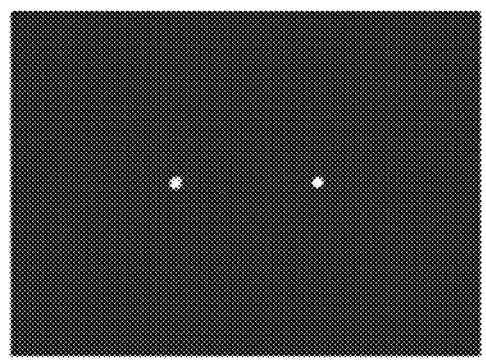
FIG. 12 is an image of a target nucleic acid of measurement 10 according to verification 7.

In order to confirm whether amplification of the target nucleic acid was performed or not after amplifying the target nucleic acid in the measurement 10, a super resolution image of an exosome was imaged with a ultra-resolution microscope. FIG. 12 shows a super resolved image of the exosome that was imaged. Note that the fluorescent stain is switched between a state in which fluorescence is generated and a state in which fluorescence is not generated, and a plurality of fluorescence images are acquired when imaging with a super-resolution microscope. A high-resolution image, that is, a super-resolution image, is acquired based on the acquired plurality of fluorescence images.

As shown in FIG. 12, the circular contour was clearly imaged and imaging of the target nucleic acid was confirmed. Hence, it was found that amplification of the target nucleic acid was carried out even when the measurement target was an exosome.

Conclusion of Verification 7

The particle measuring method according to the embodiment can also be applied to exosome measurement.

Verification 8: When the Measurement Target is *Escherichia coli*

Next, measurement samples were prepared using *E. coli* as a measurement target. However, since the target polypeptide was not labeled, only processes (A) and (B) were carried out. In the step of adjusting the temperature of process (A-10), the content of the tube was adjusted to 25° C. and held for 2 minutes. This is called measurement 11.

Figure 13A:
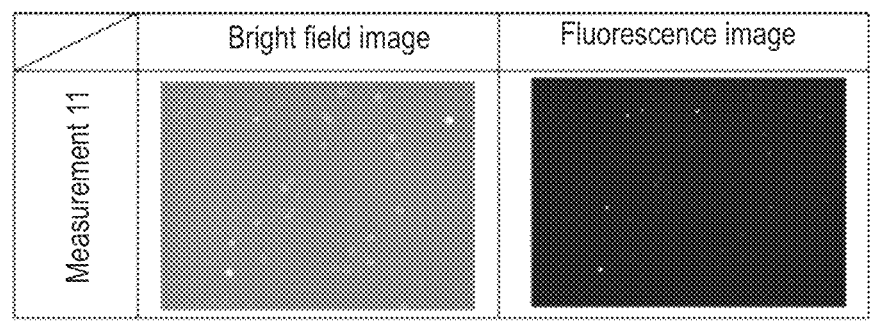
FIG. 13A is a bright field image and a fluorescence image of a target nucleic acid of measurement 11 according to verification 8.

After amplification of the target nucleic acid for measurement 11, an image of *Escherichia coli* was captured with a fluorescence microscope in order to confirm whether amplification of the target nucleic acid was performed. FIG. 13A shows a captured image of *Escherichia coli*.

The prepared measurement sample also was measured using a flow cytometer. In this way, the area of the waveform signal of the forward scattered light and the area of the waveform signal of the side scattered light were acquired for each *E. coli* contained in the measurement sample, and a scattergram shown at the top of FIG. 13B was created on the basis of each acquired parameter. In the scattergram shown in FIG. 13B, the region surrounded by the broken line is a region corresponding to the distribution of *Escherichia coli*. On the basis of *E. coli* being contained in this region, a histogram was created with the horizontal axis representing the area of the fluorescence waveform signal and the vertical axis representing the frequency as shown in the lower part of FIG. 13B. The left side of FIG. 13A is a scattergram and a histogram created based on a measurement sample immediately before the process of amplifying the target nucleic acid, that is, between the procedures (B-2) and (B-3), and the right side of FIG. 13B was created based on the measurement sample after the amplification of the target nucleic acid, that is, after procedure (B-3).

Figure 13B:
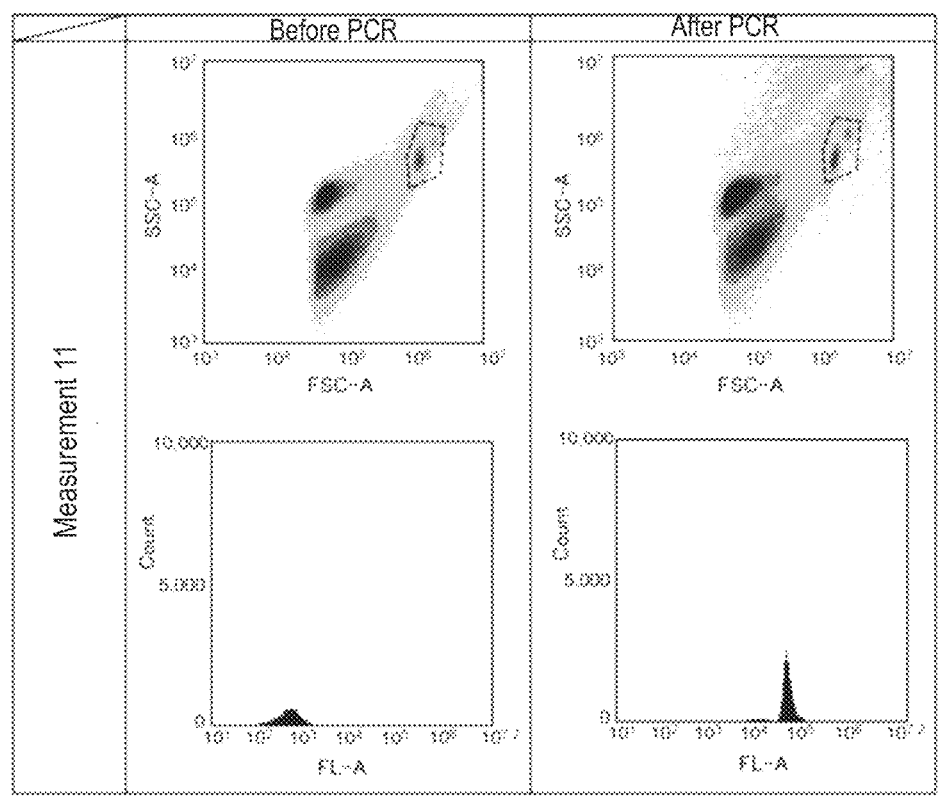
FIG. 13B shows scattergrams before and after PCR of measurement 11 according to verification 8.

From the results of FIG. 13A and FIG. 13B, it was shown that even if *E. coli* is the measurement object, the target nucleic acid can be amplified by the particle measuring method according to the embodiment.

Conclusion of Verification 8

The particle measuring method according to the embodiment can also be applied to measuring *E. coli*.

Note that the exosome used in verification 7 has attracted a great deal of attention in recent years, and studies are under way as the elucidation of exosomes leads to elucidation of the oncogenic mechanism. It is expected that the particle measuring method according to the embodiment can be applied to exosomes and can serve as a biomarker of cancer.

Verification 9: Labeling of Target Polypeptide in Particles

In the above verifications 1 to 6, the target polypeptide was present on the surface, that is, the outer surface of the particles to be measured as shown in FIG. 6C. In verification 9, whether the particle measuring method according to the embodiment can be applied even when the target polypeptide is contained inside the particle as shown in FIG. 6C was verified.

In verification 9, iPS cells were used as particles to be measured. The target nucleic acid was the GAPDH gene and the target polypeptide was the Oct 4 protein. Labeling and amplification of the target nucleic acid was carried out in the same manner as processes (A) and (B) of verification 1. Procedures for labeling the target polypeptide are shown below. In verification 9, procedure (D) is used in order to distinguish it from the procedure (C) of the verification 1. In the step of adjusting the temperature of procedure (A-10), the content of the tube also was adjusted to 25° C. and held for 2 minutes.

(D) Labeling of the Target Polypeptide

After the amplification of the target nucleic acid, a binding reaction between the target polypeptide contained and the labeled antibody was carried out in the target particle.

(D-1) 75 µL of PBS was placed in a tube, and the measurement sample was suspended.

(D-2) 5 µL of anti-Oct 4 antibody was added to the tube.

(D-3) The binding reaction between the target polypeptide and the labeled antibody was carried out at room temperature of 25° C. for 15 minutes.

A measurement sample was prepared by the above procedure. The above measurement conditions in verification 9 are designated as measurement 12. A measurement sample of measurement 12 was flowed into a flow cytometer, and images of the target nucleic acid and the target polypeptide were captured. Images in FIG. 14 are obtained by imaging measurement 12, and include in order from the left side a bright field image, an image of the target nucleic acid, an image of the target polypeptide, and the image on the far right side is a merged image of the target nucleic acid amplification image and the image of the target polypeptide. In this way, it is possible to appropriately acquire the image of the target nucleic acid and the image of the target polypeptide imaged by the flow cytometer by performing the procedure of the measurement sample according to the embodiment.

Conclusion of Verification 9

The particle measuring method according to the embodiment can also be applied to the labeling of the target polypeptide contained within the cell.

Verification 10: Labeling of Target Nucleic Acid by FISH Method

In the above verifications 1 to 9, the target nucleic acid of the particles to be measured was labeled by amplifying the target nucleic acid within the particle. In verification 10, it was verified whether the fluorescence in situ hybridization method (FISH method) can be applied in the particle measuring method according to the embodiment.

In verification 10, after amplification and labeling of the target nucleic acid with respect to the GAPDH gene, the PML gene different from the GAPDH gene was used as the target nucleic acid and the PML gene was labeled by the FISH method. That is, the labeling of the target polypeptide in step S14 in the flowchart of FIG. 1 was replaced with the labeling of the target nucleic acid by the FISH method. Amplification and labeling of the target nucleic acid with respect to the GAPDH gene was carried out in the same manner as processes (A) and (B) of verification 1. In verification 10, labeling of the target polypeptide was not performed, and procedure (E) was performed after procedure (B). Procedure (E) is shown below. Note that in the step of adjusting the temperature of procedure (A-10), the content of the tube was adjusted to 25° C. and held for 2 minutes.

(E) FISH Method

In procedure (B), the PML gene was labeled after amplification to the GAPDH gene.

(E-1) 75 µL of Hybridization Solution A (Cytocell, HA 1000 L) was added to the tube.

(E-2) 5 µL of PML Probe in Texas Red (Cytocell, MPH 6480) was added as a labeling probe to the tube.

(E-3) After adding the reagent as described above, the tube was heated at 95° C. for 5 minutes and then allowed to stand at 45° C. for 1 hour.

(E-4) After centrifuging the tube at 600 g for 3 minutes, the supernatant was removed.

(E-5) 100 µL of PBS was added to the tube, and the measurement sample was suspended.

Figure 15:
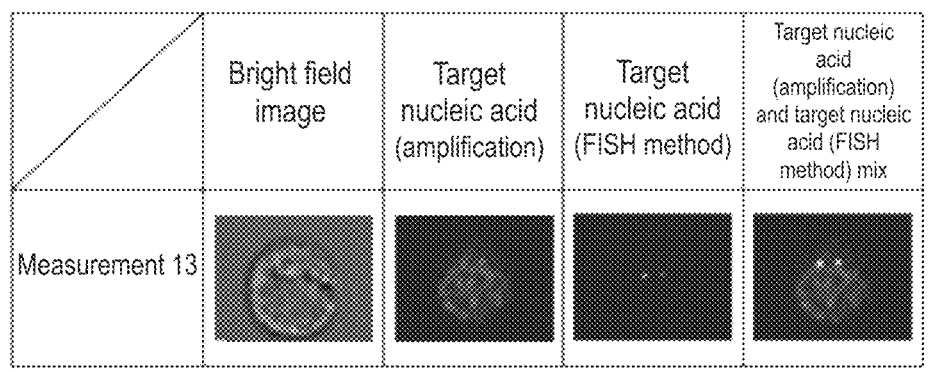
FIG. 15 shows a bright field image, an image of an amplified target nucleic acid, an image of a target nucleic acid labeled by the FISH method, a mixed image of a target nucleic acid amplified by the FISH method.
Figure 16:
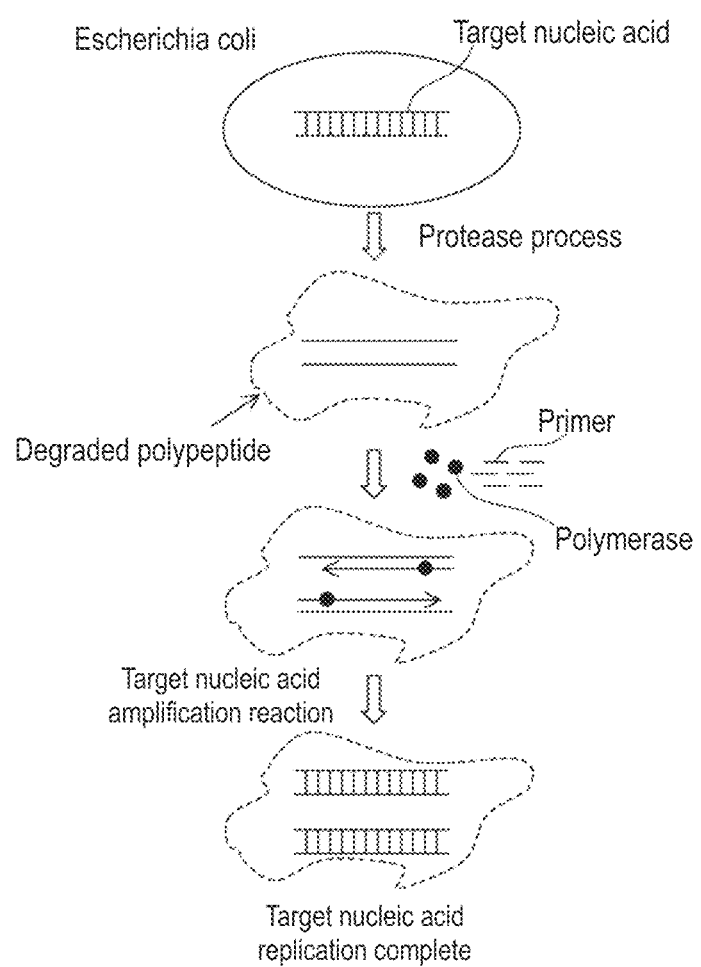
FIG. 16 is a schematic diagram illustrating related art.

A measurement sample was prepared by the above procedure. The above measurement condition in verification 10 is designated as measurement 13. A measurement sample of measurement 13 was flowed into a flow cytometer, and images of the amplified target nucleic acid and the target nucleic acid to which the FISH method was applied were captured. Images in FIG. 15 are obtained by imaging the measurement 13, and include in order from the left side a bright field image, an image of amplified target nucleic acid, an image of a target nucleic acid labeled by the FISH method, and on the right side is a merged image of the image of the amplified target nucleic acid and the image of the target nucleic acid labeled by the FISH method. In this way it is possible to appropriately acquire the image of the target nucleic acid and the image of other labeled target nucleic acid captured by flow cytometer by performing the procedure of the measurement sample according to the embodiment.

Conclusion of Verification 10]

In the particle measuring method according to the embodiment, the FISH method can be applied to the labeling of the target nucleic acid.

From the verification result of verification 10, it was found that the particle measuring method according to the embodiment can detect an abnormality of a single particle, that is, a plurality of nucleic acids contained in a cell by nucleic acid amplification and FISH method.

As described above, the FISH method is a very effective method for detecting abnormality in gene copy number. On the other hand, although nucleic acid amplification can detect gene abnormality, it is unsuitable for detection of gene copy number abnormality. That is, it is possible to detect mutations in genes which were difficult to detect by nucleic acid amplification by the FISH method, and the abnormality of genes which was difficult to detect by the FISH method can be detected by nucleic acid amplification. In this way, when nucleic acid amplification and FISH method are simultaneously used for one cell, each detection method performs detection of abnormality well, and as a result, gene abnormalities can be detected so as to compensate for the weaknesses of each method. Based on these findings, the detection method in which nucleic acid amplification and FISH method are simultaneously performed on one cell can detect genetic abnormality more accurately, and is expected to become a detection method with high detection clinical value that can obtain more reliable information.

Anti-HER2 therapy is also performed for breast cancer patients whose HER2 gene is amplified. However, about 20% of the patients in which the HER2 gene is amplified are said to have PIK3Ca gene mutation. As described above, there is a report that in patients in which the HER2 gene is amplified and further the PIK3Ca gene mutation occurs, the complete remission rate decreases by half. Therefore, by using the FISH method for HER2 gene and by in situ PCR for PIK3Ca gene, it can be determined whether anti-HER2 therapy is appropriately effective for breast cancer patients, and can aid in deciding treatment policy.

As described above, it is a very useful method in clinical diagnosis to detect abnormality by nucleic acid amplification and FISH method for plural nucleic acids contained in one particle, that is, a cell.

Note that, in the verification 10, the GAPDH gene corresponds to the "target nucleic acid" described in the claims, and the PML gene corresponds to the "other target nucleic acid" described in the claims.

In verification 10, Although the target polypeptide was not labeled, the measurement sample may be prepared by procedure (C) in the same manner as in verification 1 after amplification of the target nucleic acid and labeling with other target nucleic acids by the FISH method. Even when another target nucleic acid is labeled by the FISH method as described with reference to FIG. 6, the polypeptide on the surface of the particle is not completely decomposed, and the gap is expanded while maintaining its shape. Therefore, labeling of the target polypeptide can be carried out. The target nucleic acid, the other target nucleic acid, and the labeling substance that labels each of the target polypeptides also is referred to as "first labeling substance", "second labeling substance", and "3 labeling substance". Also, the target polypeptide may be contained inside the particle based on the verification result of verification 9.

Note that in the verification 10, another target nucleic acid was labeled by the FISH method after amplification of the target nucleic acid. Each target nucleic acid may be labeled even when this order is reversed.

In this way, for each particle to be measured, detection of particle abnormality can be detected according to the particle measuring method of the embodiment by appropriately combining the amplification of the target nucleic acid, the labeling of the other target nucleic acid, and the labeling of the target polypeptide.

With respect to the particles to be measured, a combination of labeling and amplification of the target nucleic acid and labeling of the target polypeptide, or combination of labeling and amplification of the target nucleic acid and labeling of the other target nucleic acid were verified in the above verifications; however, the particle measuring method according to the embodiment makes it possible to simultaneously perform labeling and amplification of a target nucleic acid, labeling of a target polypeptide, and labeling of another target nucleic acid simultaneously, and then performing measurements.

An example of such is diagnosis of breast cancer. In the diagnosis of breast cancer, abnormalities of intracellular protein Ki67 and the HER2 gene and PIK3Ca gene described above are investigated. Conventionally, Ki67 has been detected separately by immunostaining, HER2 gene by FISH method, PIK3Ca gene by in situ PCR, respectively. However, with the particle measuring method according to the embodiment, it is possible to simultaneously measure these proteins and genes. By measuring these at the same time, the measurement work efficiency can be improved. Hence, it is possible to present diagnosis results to breast cancer patients at an early stage. According to the method of the present invention, since it is possible to grasp the state of Ki67, HER2 gene, PIK3Ca gene on one cell, it is thought that there is a possibility of creating new clinical value from these relationships.

What is claimed is:

1. A particle measuring method, comprising:
labeling and amplifying, within a particle contained in a sample, a first target nucleic acid included in the particle by performing a polymerase chain reaction (PCR) including multiple cycles of a temperature control, wherein the sample is not treated with protease;
labeling one or both of a target polypeptide and a second target nucleic acid different from the first target nucleic acid of the particle in the sample after performing the PCR, wherein the target polypeptide is labeled with an antibody and the second target nucleic acid is labeled with FISH probe; and
measuring the labeled first target nucleic acid and one or both of the labeled target polypeptide and the labeled second target nucleic acid of the particle in the sample by a single run of the sample in a flow cytometer.

2. The particle measuring method according to claim 1, wherein
in the labeling of one or both of the target polypeptide and the second target nucleic acid, a target polypeptide on the surface of the particle is labeled; and
in the measuring of the labeled first target nucleic acid and one or both of the labeled target polypeptide and the second target nucleic acid, the labeled first target nucleic acid, one or both of the labeled target polypeptide, and the labeled second target nucleic acid are measured.

3. The particle measuring method according to claim 1, wherein
the measuring of the labeled first target nucleic acid and one or both of the labeled target polypeptide and the second target nucleic acid is performed, after performing the labeling and amplifying the first target nucleic acid and performing labeling one or both of the target polypeptide and the second target nucleic acid.

4. The method according to claim 1, wherein
the measuring the labeled first target nucleic acid and one or both of the labeled target polypeptide and the second target nucleic acid comprises capturing an image of the particle.

5. The particle measuring method according to claim 1, wherein the measuring the labeled first target nucleic acid and one or both of the labeled target polypeptide and the second target nucleic acid included in the particle comprises:
flowing the labeled first target nucleic acid and one or both of the labeled target polypeptide and the labeled second target nucleic acid through the flow cell; and
imaging the light obtained by irradiating light on the liquid in the flow cell.

6. The method according to claim 1, further comprising:
analyzing a captured image after the measuring the labeled first target nucleic acid and one or both of the labeled target polypeptide and the second target nucleic acid.

7. The method according to claim 1, wherein
the first target nucleic acid is labeled with a first labeling substance, and one or both of the target polypeptide is labeled with a second labeling substance different from the first labeling substance and the second target nucleic acid is labeled with a third labeling substance different from the first labeling substance and the second labeling substance.

8. The particle measuring method according to claim 1, wherein
the sample is treated with a polymerase.

9. The particle measuring method according to claim 1, wherein
the sample is treated with a primer.

10. The method according to claim 1, wherein
the labeling and amplifying the first target nucleic acid is followed by the labeling one or both of the target polypeptide and the second target nucleic acid.

11. The particle measuring method according to claim 1, wherein
in the labeling of one or both of the target polypeptide and the second target nucleic acid, the target polypeptide is labeled with a labeling antibody that specifically binds to the target polypeptide.

12. The particle measuring method according to claim 1, wherein
in the labeling of one or both of the target polypeptide and the second target nucleic acid, the target polypeptide contained in the particle is labeled; and
in the measuring of the labeled first target nucleic acid and one or both of the labeled target polypeptide and the second target nucleic acid, the labeled first target nucleic acid and the labeled target polypeptide are measured.

13. The particle measuring method according to claim 1, wherein
in the labeling of one or both of the target polypeptide and the second target nucleic acid, the second target nucleic acid is labeled; and
in the measuring of the labeled first target nucleic acid and one or both of the labeled target polypeptide and the second target nucleic acid, the second target nucleic acid is measured.

14. A sample processing method, comprising:
preparing a mixed solution, substantially not containing protease, containing particles and a labeled probe that binds to a target nucleic acid in the particles, wherein the particles are included in a sample, and the sample is not treated with the protease; and
amplifying a target nucleic acid included in the particles by performing a polymerase chain reaction (PCR) including multiple cycles of a temperature control.

* * * * *